US009572610B2

(12) United States Patent
Cornelius et al.

(10) Patent No.: US 9,572,610 B2
(45) Date of Patent: Feb. 21, 2017

(54) MANDIBULAR BONE PLATE

(71) Applicant: DePuy Synthes Product, Inc., Raynham, MA (US)

(72) Inventors: Carl-Peter Cornelius, Ulm (DE); Robert Schoutens, Oberdorf (CH); Razvan Gheorghe, Oberdorf (CH); Azagen Mootien, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 256 days.

(21) Appl. No.: 13/827,184

(22) Filed: Mar. 14, 2013

(65) Prior Publication Data
US 2014/0277174 A1    Sep. 18, 2014

(51) Int. Cl.
*A61B 17/80* (2006.01)
*A61B 17/17* (2006.01)
*A61B 17/16* (2006.01)
*A61B 17/86* (2006.01)

(52) U.S. Cl.
CPC ....... *A61B 17/8071* (2013.01); *A61B 17/1673* (2013.01); *A61B 17/176* (2013.01); *A61B 17/8023* (2013.01); *A61B 17/8057* (2013.01); *A61B 17/8085* (2013.01); *A61B 17/86* (2013.01); *A61B 17/1728* (2013.01)

(58) Field of Classification Search
CPC  A61B 17/8071; A61B 17/8085; A61F 2/2803
See application file for complete search history.

(56) References Cited

U.S. PATENT DOCUMENTS

| 5,087,259 | A   | 2/1992 | Krenkel |
|---|---|---|---|
| 6,423,068 | B1  | 7/2002 | Reisberg et al. |
| 6,730,091 | B1  | 5/2004 | Pfefferle et al. |
| 2006/0085000 | A1* | 4/2006 | Mohr et al. ..................... 606/69 |
| 2008/0097432 | A1* | 4/2008 | Schulze ............ A61B 17/8085 606/86 A |

(Continued)

FOREIGN PATENT DOCUMENTS

DE    102005032026 B3    12/2006

OTHER PUBLICATIONS

Bowerman et al., "A Universal Kit in Titanium for Immediate Replacement of the Resected Mandible," Br. J. Oral Surg., 1968, 6(3), 223-228.

(Continued)

*Primary Examiner* — David Bates
*Assistant Examiner* — Olivia C Chang
(74) *Attorney, Agent, or Firm* — Baker & Hostetler LLP

(57) ABSTRACT

A mandibular bone plate can include a body that defines a bone facing surface, an outer surface that is opposite the bone facing surface, and a plurality of bone anchor holes that extend through the body from the bone facing surface to the outer surface. The body can include a chin portion and first and second extension portions that extend from the chin portion such that the bone facing surface of the chin portion faces the inferior surface of the mandible when the mandibular bone plate is attached to the mandible and the bone facing surfaces of the first and second extension portions at least partially face the lingual surface of the mandible when the mandibular bone plate is attached to the mandible.

37 Claims, 19 Drawing Sheets

(56) References Cited

U.S. PATENT DOCUMENTS

2008/0294165 A1* 11/2008 Cunliffe ............ A61B 17/7004
   606/70
2010/0131013 A1   5/2010 Ralph et al.
2010/0305569 A1* 12/2010 Leuenberger ...... A61B 17/8085
   606/70
2011/0046682 A1   2/2011 Stephan et al.

OTHER PUBLICATIONS

Madsen et al., "A Biomechanical Comparison of 2 Techniques for Reconstructing Atrophic Edentulous Mandible Fractures," J. Oral Maxillofac. Surg., Mar. 2006, 64(3), 457-465.
Novelli et al., "Surgical Treatment of the Atrophic Mandibular Fractures by Locked Plates Systems: Our Experience and a Literature Review," Craniomaxillofac Trauma Reconstruction, Jan. 2012, 5(2), 65-74.
Schuller-Gotzburg et al., "The caudal mandibular reconstruction plate: a radiographic and histologic study of an autopsy specimen," Br. J. Oral Maxillofac. Surg., Jun. 1992, 30(3), 174-179.
Sutter et al., "Titanium-coated hollow screw and reconstruction plate system for bridging of lower jaw defects: biomechanical aspects," Int. J. Oral Maxillofac. Surg., Aug. 1988, 17(4), 267-274.
Tiwana et al., "Management of Atrophic Edentulous Mandibular Fractures: The Case for Primary Reconstruction With Immediate Bone Grafting," J. Oral Maxillofac. Surg., Apr. 2009, 67(4), 882-887.

* cited by examiner

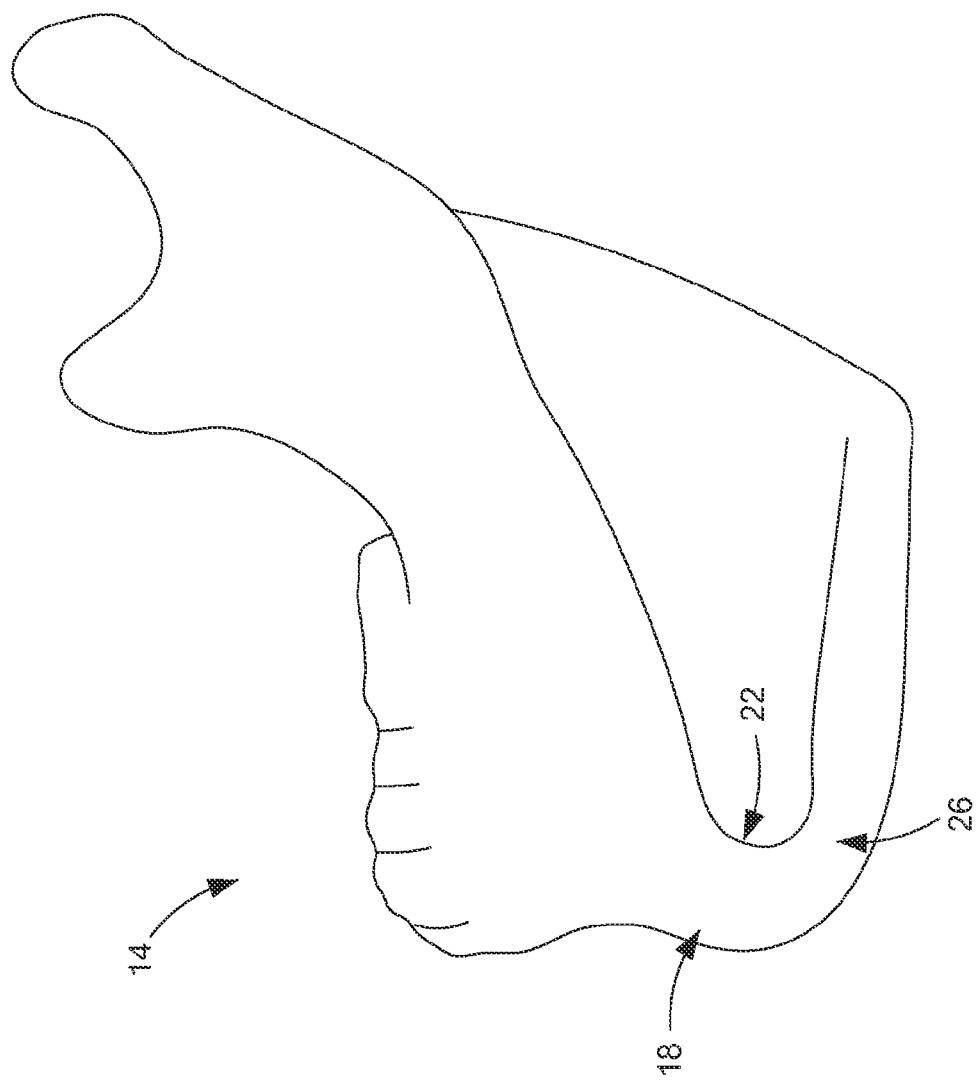

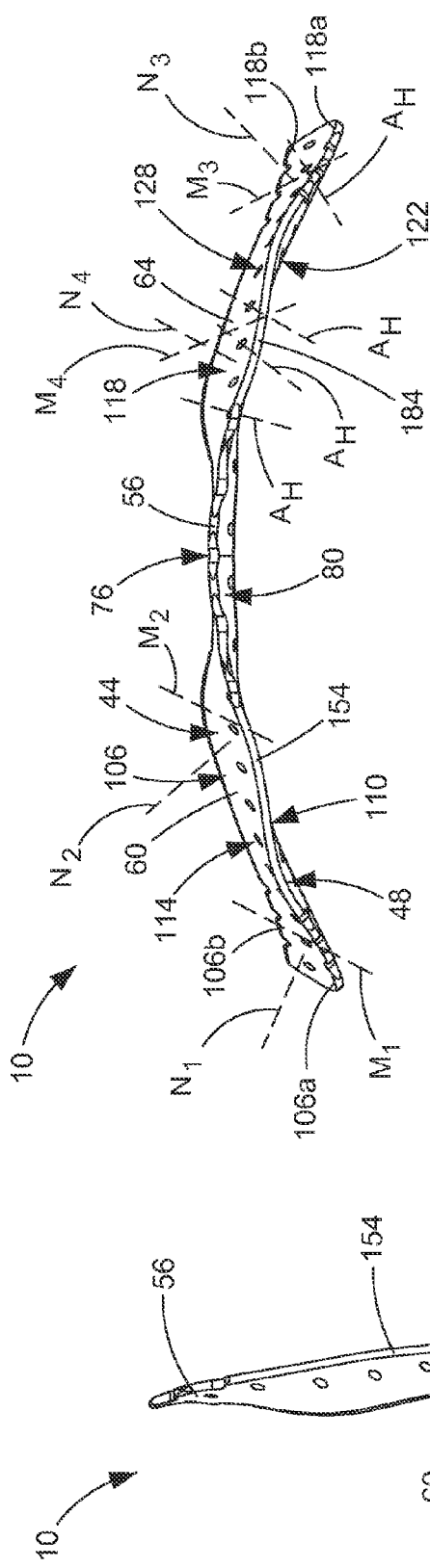

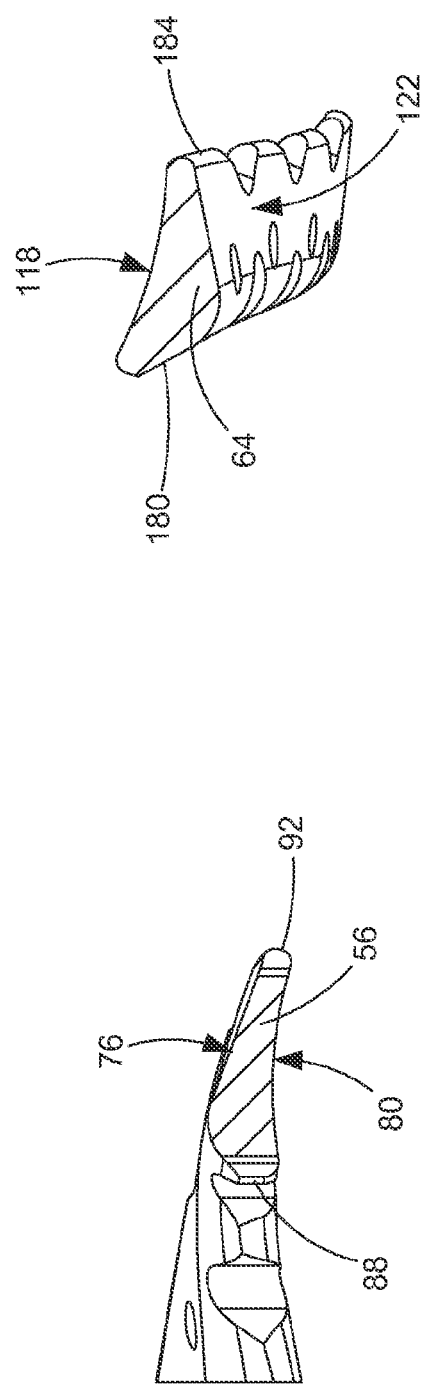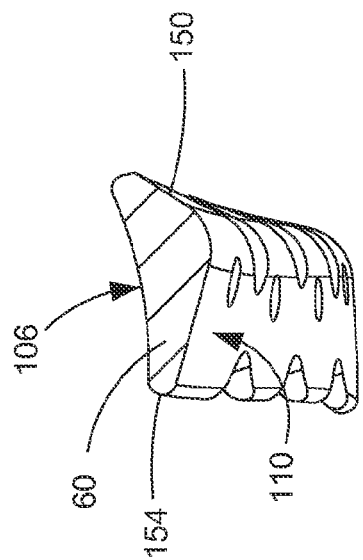

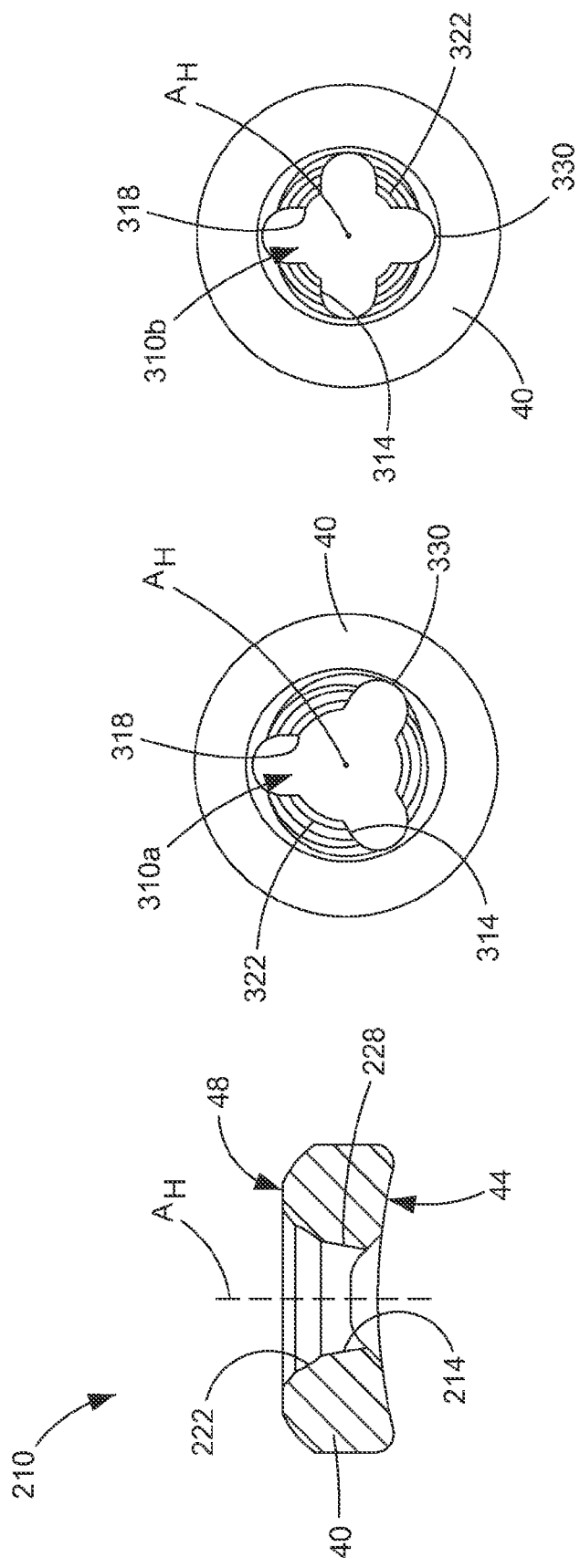

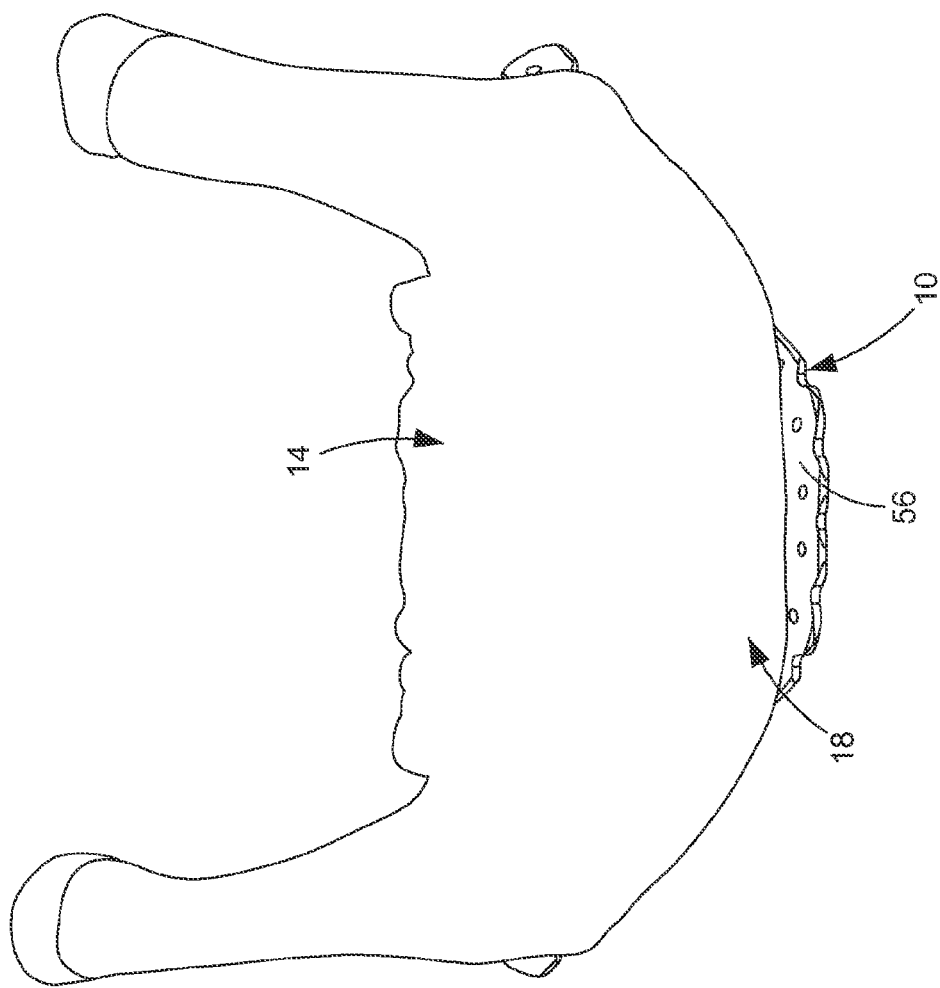

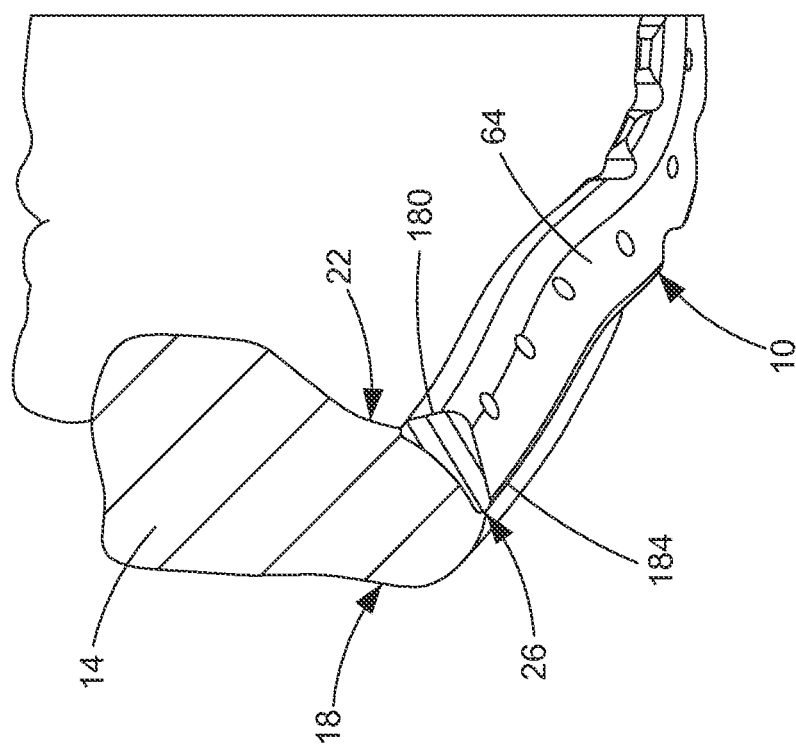

MANDIBULAR BONE PLATE

BACKGROUND

An individual may require a mandible reconstruction due to trauma, atrophy, or a tumor. To remove a tumor, the surgeon may cut the mandible on either side of the tumor thereby separating the tumor from the mandible. Once the tumor is removed, the mandible is separated into a first part and a second part. If needed, the first part and/or the second part may be repositioned and screws and plates are used to fix the first part and the second part together until natural bone healing takes place.

The mandibular bone plates currently used are shaped so as to be attached to a buccal surface, and in some cases on an inferior surface of the mandible. As a result, these plates have relatively high profiles which may cause irritation to the surrounding soft tissue such as for example to the surrounding blood vessels, muscles, nerves, and skin, and may also cause palpable cosmetic deformities. Furthermore, the adaptation of these plates to facilitate an anatomical placement may result in degraded performance and/or reduced fatigue life.

SUMMARY

In an embodiment, a mandibular bone plate that is configured to be attached to a mandible that defines a buccal surface, a lingual surface, and an inferior surface that joins the buccal surface to the lingual surface, can include a curved chin portion having a first end and a second end and a first extension portion that extends from the first end along a first axis and is elongate along the first axis so as to define a proximal end that is proximate the first end and a distal end that is spaced from the proximal end along the first axis. The first extension portion can define a first bone facing surface, a first outer surface that is opposite the first bone facing surface, and a plurality of bone anchor holes that extend from the first bone facing surface to the first outer surface. The first bone facing surface can have an inferior end and a superior end that is spaced from the inferior end along a first direction that is perpendicular to the first axis. And, the first extension portion can be oriented such that a line that is tangential to the inferior end and to the superior end of the first bone facing surface along the first direction at a distal portion of the first extension portion is rotated about the first axis relative to a line that is tangential to the inferior end and to the superior end of the first bone facing surface along the first direction at a proximal portion of the first extension portion so that the first bone facing surface is configured to abut at least a portion of at least two of the buccal, lingual and inferior surfaces of the mandible when the mandibular bone plate is attached to the mandible.

In another embodiment, a mandibular bone plate can include a body that defines a bone facing surface, an outer surface that is opposite the bone facing surface, and a plurality of bone anchor holes that extend through the body from the bone facing surface to the outer surface. The body can include a chin portion and first and second extension portions that extend from the chin portion such that the bone facing surface of the chin portion faces the inferior surface of the mandible when the mandibular bone plate is attached to the mandible and the bone facing surfaces of the first and second extension portions at least partially face the lingual surface of the mandible when the mandibular bone plate is attached to the mandible.

In another embodiment, a method of affixing a bone plate to a mandible having a buccal surface, a lingual surface, and an inferior surface that extends from the lingual surface to the buccal surface, can include the steps of exposing the inferior and lingual surfaces of the mandible; positioning a bone plate against the mandible such that portions of the bone plate abut the lingual surface of the mandible; and affixing the bone plate to the mandible with a plurality of bone anchors.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 1A is a perspective view of an example mandible that defines a buccal surface, a lingual surface, and an inferior surface that extends from the lingual surface to the buccal surface;

FIG. 2B is a side elevation view of the mandibular bone plate shown in FIG. 2A;

FIG. 2C is a front elevation view of the mandibular bone plate shown in FIG. 2A;

FIG. 2D is a rear elevation view of the mandibular bone plate shown in FIG. 2A;

FIG. 2G is a cross-sectional view of the chin portion of the mandibular bone plate shown in FIG. 2F through the line 2G-2G;

FIG. 2H is a cross-sectional view of the first extension portion of the mandibular bone plate shown in FIG. 2F through the line 2H-2H;

FIG. 2I is a cross-sectional view of the second extension portion of the mandibular bone plate shown in FIG. 2F through the line 2I-2I;

FIG. 3A is a cross-sectional view showing an embodiment of a bone anchor hole of the mandibular bone plate shown in FIG. 2A, the bone anchor hole being configured as a variable angle non-locking bone anchor hole;

FIG. 3B is a top plan view showing another embodiment of a bone anchor hole of the mandibular bone plate shown in FIG. 2A, the bone anchor hole being configured as a variable angle locking bone anchor hole;

FIG. 3C is a top plan view showing yet another embodiment of a bone anchor hole of the mandibular bone plate shown in FIG. 2A, the bone anchor hole being configured as a variable angle locking bone anchor hole;

FIG. 5C is a front elevation view of the mandibular bone plate shown in FIG. 2A attached to the mandible shown in FIG. 1A;

FIG. 5F is a cross-sectional view of the mandibular bone plate attached to the mandible shown in FIG. 5D through the line 5F-5F;

DETAILED DESCRIPTION OF ILLUSTRATIVE EMBODIMENTS

Figure 1B:
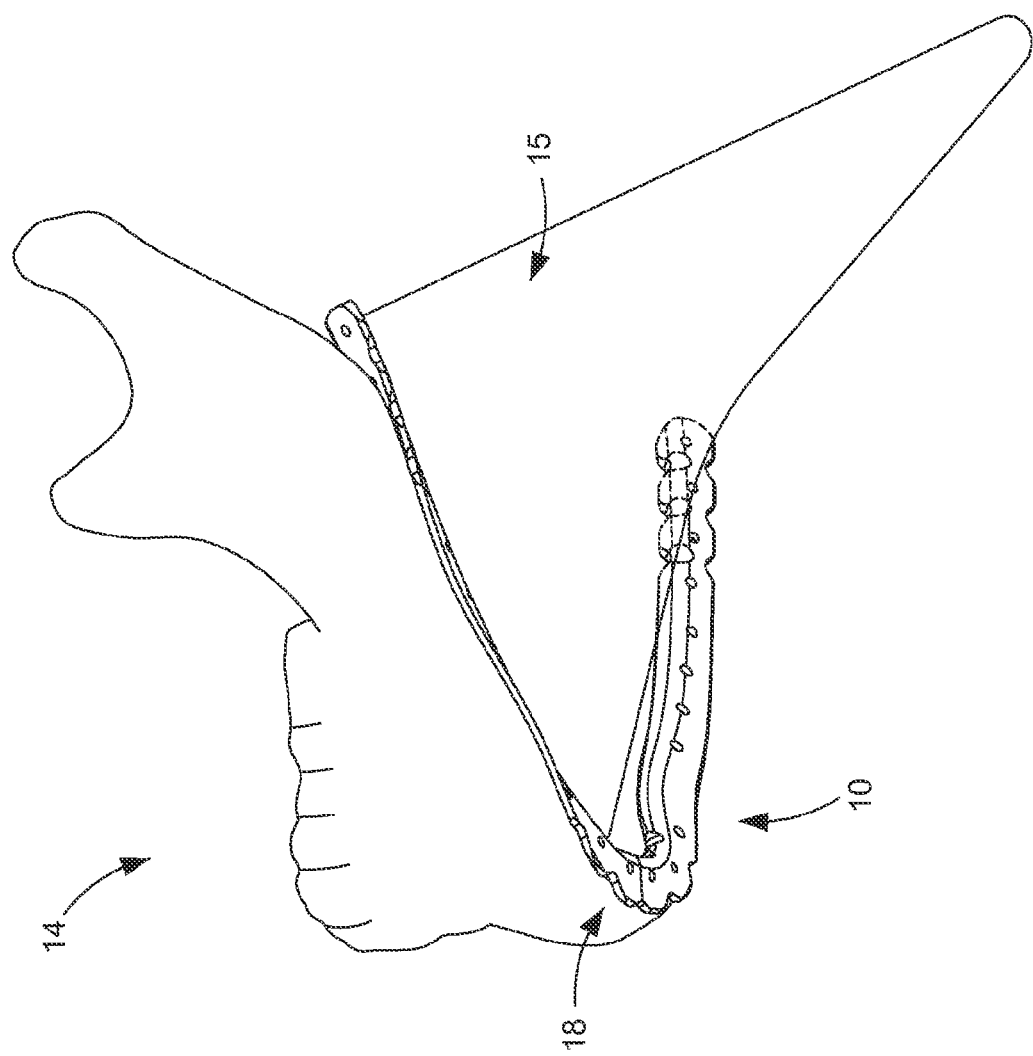
FIG. 1B is a perspective view of a mandibular bone plate in accordance with an embodiment attached to the mandible shown in FIG. 1A, the mandibular bone plate being configured to abut portions of the lingual surface of the mandible when attached to the mandible.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

As shown in FIGS. 1A and 1B, a mandibular bone plate 10 can be configured to be affixed to a mandible 14 to thereby correct certain conditions of the mandible related to structure, growth, Temporomandibular Joint Disorder (TMJ disorder) or to correct orthodontic problems. As shown in FIG. 1A, the mandible 14 defines an outer or buccal surface 18, an inner or lingual surface 22, and a lower or inferior surface 26 that extends from the lingual surface 22 to the buccal surface 18. As shown in FIG. 1B, the mandibular bone plate 10 is configured to be affixed to the mandible 14 such that portions of the mandibular bone plate 10 abut the lingual surface 22 of the mandible 14. As shown in FIG. 1B, the mandibular bone plate 10 can be further configured to be affixed to the mandible 14 such that portions of the mandibular bone plate 10 also face the inferior surface 26 of the mandible 14 to thereby avoid certain tissue such as for example a throat portion 15. It should be appreciated, however, that the mandibular bone plate 10 can be configured to be positioned to abut both the buccal and inferior surfaces 18 and 26 or all three surfaces 18, 22, and 26 of the mandible 14 as desired. Because of the positioning and geometry of the mandibular bone plate 10, at least the palpability of the bone plate 10 can be reduced, as compared to bone plates that are attached solely to the buccal or inferior surfaces 18 and 26 of the mandible 14. It should be appreciated, that the mandible 14 is for illustration purposes only and that the mandibular bone plate 10 can be attached to any type of mandible in any type of condition. For example, the mandibular bone plate 10 can be configured to be attached to an atrophic mandible. It should further be appreciated that the mandibular bone plate 10 can be configured to be affixed to the mandible 14 for any desired reason and/or to correct/treat any type of condition, fracture, or reconstruction.

Referring to FIGS. 2A-2I, the mandibular bone plate 10 and various components of the bone plate are described herein extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. When the mandibular bone plate 10 is implanted onto a mandible, such as the mandible 14, the transverse direction T extends vertically generally along the superior-inferior (or cranial-caudal) direction, while the plane defined by the longitudinal direction L and lateral direction A extends horizontally, generally in the anatomical plane defined by the medial-lateral direction and the anterior-posterior direction. Accordingly, the directional terms "vertical" and "horizontal" are used to describe the mandibular bone plate 10 and its components as illustrated merely for the purposes of clarity and illustration.

Figure 2A:
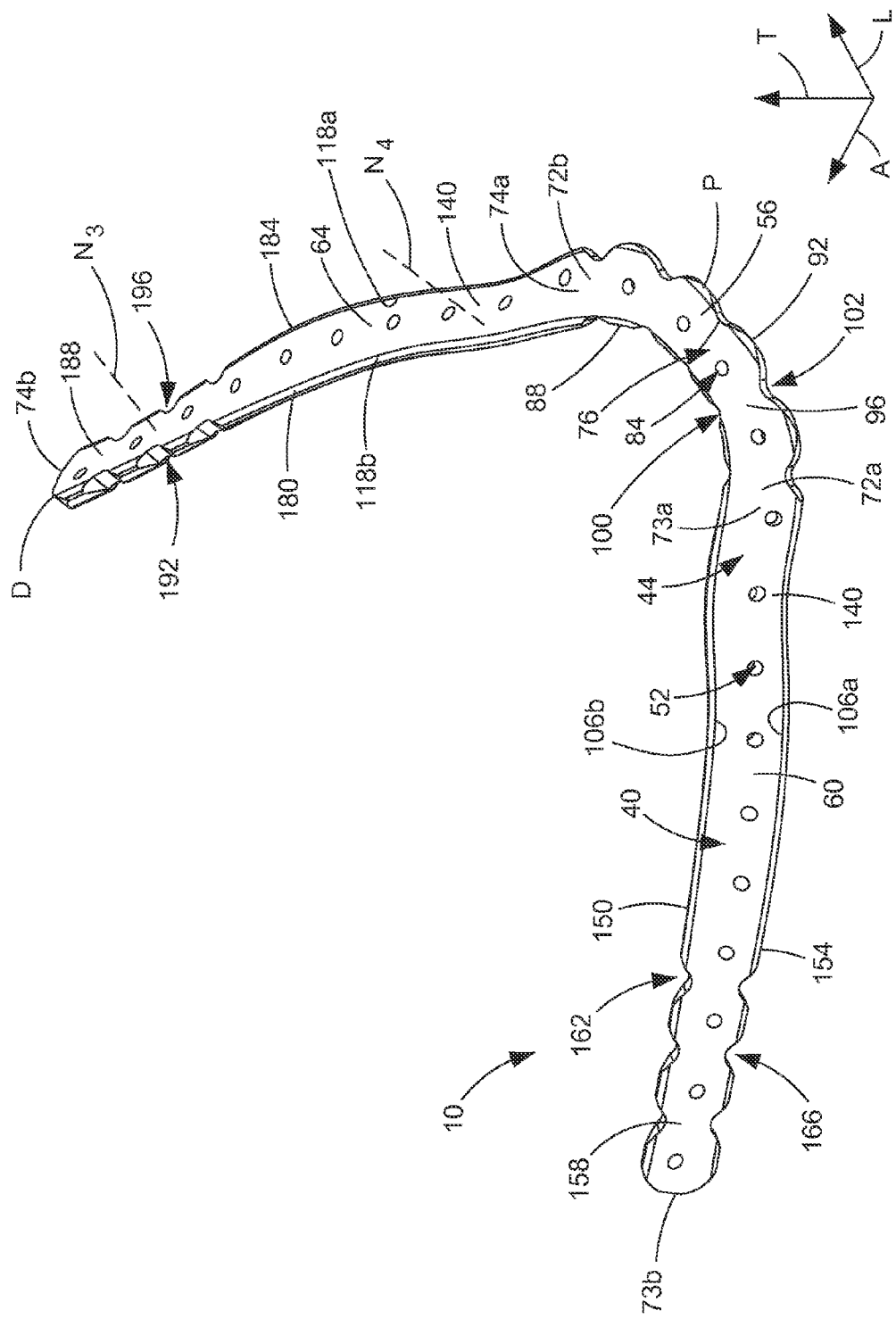
FIG. 2A is a top perspective view of the mandibular bone plate shown in FIG. 1B, the mandibular bone plate including a body that has a chin portion, a first extension portion that extends from the chin portion along a first axis and a second extension portion that extends from the chin portion along a second axis, the body defining a bone facing surface, an outer surface that is opposite the bone facing surface, and a plurality of bone anchor holes that extend through the body from the bone facing surface to the outer surface.
Figure 2E:
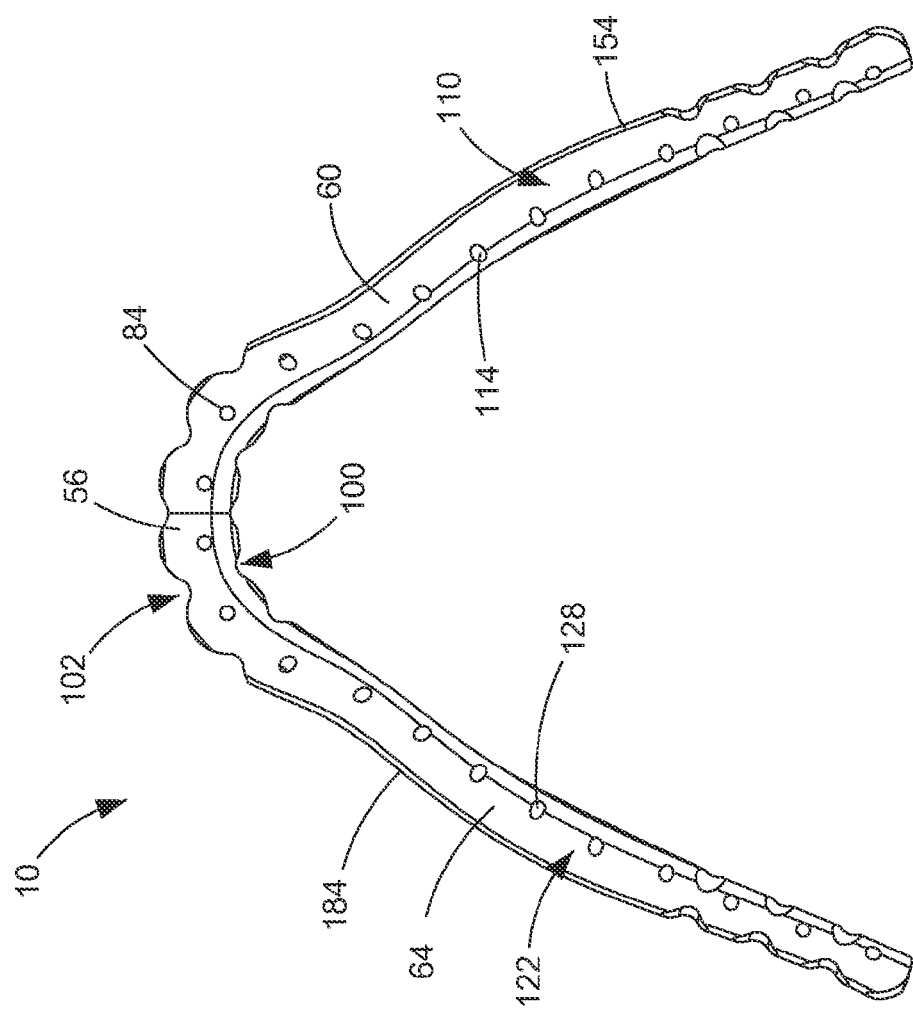
FIG. 2E is a bottom plan view of the mandibular bone plate shown in FIG. 2A.

As shown in FIG. 2A, the mandibular bone plate 10 can include a substantially v-shaped body 40 that defines a proximal end P and a distal end D. The v-shaped body can further define a bone facing surface 44, an outer surface 48 that is opposite the bone facing surface 44 at least partially along the transverse direction T, and a plurality of bone anchor holes 52 that extend through the body 40 from the bone facing surface 44 to the outer surface 48. The mandibular bone plate 10, and in particular, the v-shaped body 40 can include a chin portion 56, a first extension portion 60 that extends from the chin portion 56 generally along the lateral direction A, and a second extension portion 64 that extends from the chin portion 56 generally along the lateral direction A. The chin portion 56, first extension portion 60, and the second extension portion 64 are oriented such that the bone facing surface 44 of the chin portion 56 faces the inferior surface 26 of the mandible 14 when the mandibular bone plate 10 is attached to the mandible 14 and the bone facing surfaces 44 of the first and second extension portions 60 and 64 at least partially face the lingual surface 22 of the mandible 14 when the mandibular bone plate 10 is attached to the mandible 14. It should be appreciated, however, that the chin portion 56, the first extension portion 60, and the second extension portion 64 can be oriented such that the bone plate 10 abuts or otherwise faces at least two of the buccal, lingual, and inferior surfaces 18, 22, and 26. It should further be appreciated, that the body 40 can have any general shape as desired. For example, the body 40 could be substantially U-shaped as desired, or substantially J-shaped as desired. Therefore it should further be appreciated, that the bone plate 10 can be configured as one J-shaped plate or as a pair of J-shaped plates each having a chin portion and a respective extension. The orientation of the bone facing surface 44 can be anatomically derived. For example, the orientation of the bone facing surface 44 can be derived by taking statistics of a plurality of mandibles 14 to thereby derive an orientation that would correspond to a majority of mandibles. It should be appreciated, however, that the orientation of the bone facing surface 44 can be derived using any method as desired. The mandibular bone plate 10 can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), bioresorbable and/composite materials. A coating may be added or applied to the mandibular bone plate 10 to improve physical or chemical properties or to provide medications. Examples of coatings include plasma-sprayed titanium, Hydroxyapatite, or antibacterial coatings.

With continued reference to FIGS. 2A and 2C-2F, the chin portion 56 can be curved along the longitudinal direction L and has a first end 72a and a second end 72b that is spaced from the first end 72a along the longitudinal direction L. As shown in FIGS. 2A-2F, the chin portion 56 can define a chin bone facing surface 76 of the bone facing surface 44, an outer surface 80 that is opposite the chin bone facing surface 76, and at least one bone anchor hole 84 of the bone anchor holes 52, such as a plurality of bone anchor holes 84, that extend through the chin portion 56 from the chin bone facing surface 76 to the outer surface 80. As shown in FIG. 1B, the chin portion 56 can be flat such that the chin bone facing surface 76 faces and is spaced from the inferior surface 26 of the mandible 14 when the mandibular bone plate 10 is attached to the mandible 14. It should be appreciated, however, that the chin portion 56 can have any configuration as desired. For example, the chin portion 56 can include undulations or otherwise be configured such that at least a portion of the chin bone facing surface 76 faces the lingual surface 22 of the mandible 14 when the mandibular bone plate 10 is attached to the mandible 14 and/or such that at least a portion of the chin bone facing surface 76 abuts the inferior surface 26 of the mandible 14.

Figure 2F:
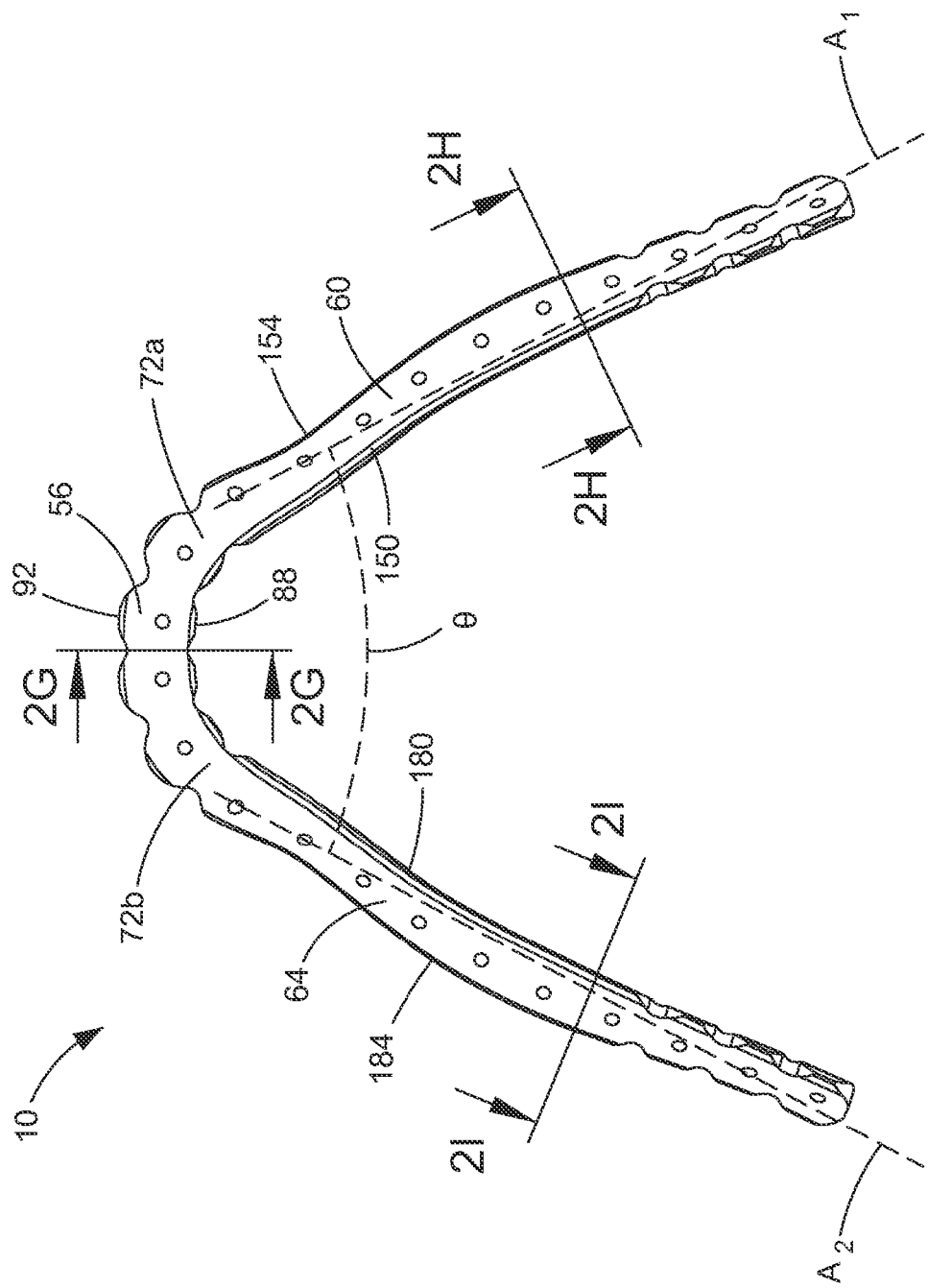
FIG. 2F is a top plan view of the mandibular bone plate shown in FIG. 2A.

As shown in FIGS. 2A, 2F and 2G, the chin portion 56 can further define a first side surface 88 that extends from the outer surface 80 to the chin bone facing surface 76 and a second side surface 92 that is opposite the first side surface 88 and extends from the outer surface 80 to the chin bone facing surface 76. As shown in FIG. 2G, the first and second side surfaces 88 and 92 can be convex or otherwise curved. As shown in FIG. 2F, the chin portion 56 can further include a plurality of weakened portions 96 between adjacent bone anchor holes 84. The weakened portions 96 are configured to allow the chin portion 56 to be bent during implantation of the mandibular bone plate 10. In particular, each weakened portion 96 is defined by at least a first recess 100 that extends into the first side surface 88 and a second recess 102 that extends into the second side surface 92 opposite the first recess 100. In the illustrated embodiment, the chin portion 56 includes six bone anchor holes 84 and four weakened portions 96. It should be appreciated, however, that the chin portion 56 can include any number of bone anchor holes 84 as desired and any number of weakened portions 96 as desired. It should be further appreciated, that the weakened portions 96 can be defined by other structure. For example, the weakened portions 96 can be defined by recesses formed in the chin bone facing surface 76 and/or the outer surface 80.

With continued reference to FIG. 2G, at least a portion of the chin portion 56, up to the entirety of the chin portion 56 can be substantially triangular shaped in cross-section. That is, the chin portion 56 can taper from the first side surface 88 to the second side surface 92. Therefore a thickness of the chin portion 56 at the second side surface 92 can be less than that of the chin portion 56 at a center of the chin portion 56 between the first and second side surfaces 88 and 92. It should be appreciated, however, that the chin portion 56 can have any shape in cross-section as desired. For example, the chin portion 56 can be rectangular shaped in cross-section as desired. It should be further appreciated, that substantially triangular shaped means to have either a triangular shape or the general appearance of a triangle. For example, while the chin portion 56 has first and second side surfaces 88 and 92, because of the taper, the chin portion 56 substantially defines a triangle in cross-section.

Now in reference to FIGS. 2A-2F, the first extension portion 60 generally extends from the first end 72a along a first axis $A_1$ and is elongate along the first axis $A_1$, and the second extension portion 64 generally extends from the second end 72b along a second axis $A_2$ and is elongate along the second axis $A_2$. The first extension portion 60 defines a proximal end 73a that is proximate the first end 72a and a distal end 73b that is spaced from the proximal end 73a along the first axis $A_1$. The second extension portion 64 defines a proximal end 74a that is proximate the second end 72b and a distal end 74b that is spaced from the proximal end 74a along the first axis $A_2$. As shown in FIG. 2C, the first extension portion 60 defines a first bone facing surface 106 of the bone facing surface 44, a first outer surface 110 that is opposite the first bone facing surface 106, and a plurality of bone anchor holes 114 of the plurality of bone anchor holes 52 that extend from the first bone facing surface 106 to the first outer surface 110. The second extension portion 64 defines a second bone facing surface 118 of the bone facing surface 44, a second outer surface 122 that is opposite the first bone facing surface 118, and a plurality of bone anchor holes 128 of the plurality of bone anchor holes 52 that extend from the second bone facing surface 118 to the second outer surface 122. The chin bone facing surface 76, the first bone facing surface 106, and the second bone facing surface 118 are coincident so as to define the bone facing surface 44 of the body 40 such that the bone facing surface 44 is continuous. Similarly, the outer surfaces 80, 110, and 122 are coincident so as to define the outer surface 48 of the body 40 such that the outer surface 48 is continuous. It should be appreciated, however, that the surfaces 76, 106, and 118 and/or the surfaces 80, 110, and 122 can be interrupted so as to provide minimal or reduced contact with the bone. For example, any of the surfaces 76, 80, 106, 110, 118, and 122 can define a scallop or recess that interrupts the continuity of the surfaces.

As shown in FIG. 2A, the first bone facing surface 106 defines an inferior end 106a and a superior end 106b that is spaced from the inferior end 106a along a first direction that is perpendicular to the first axis $A_1$. Similarly the second bone facing surface 118 defines an inferior end 118a and a superior end 118b that is spaced from the inferior end 106a along a second direction that is perpendicular to the second axis $A_2$. The first and second directions should be taken along the shortest distance between the respective inferior and superior ends. It should be appreciated, that the first and second directions will change along the length of the first and second extension portions 60 and 64 because the orientation of the first and second extension portions 60 and 64 changes along their lengths. That is the first and second directions will be a direction that takes the shortest path from the inferior end to the superior end that is perpendicular to the respective axes at any point along the first and second extension portions 60 and 64.

As shown in FIG. 2F, the first and second extension portions 60 and 64 are generally spaced from each other along the longitudinal direction L and the first and second axes $A_1$ and $A_2$ are angularly offset from each other such that an angle θ is defined between the first and second axes $A_1$ and $A_2$. Therefore, the first and second extension portions 60 and 64 diverge as they extend distally from the chin portion 56. It should be appreciated that the angle θ can be any angle as desired.

As shown in FIGS. 2B-2D, the first extension portion 60 is twisted counterclockwise about the first axis $A_1$ relative to the curved chin portion 56 such that the first bone facing surface 106 is configured to abut at least a portion of the lingual surface 22 of the mandible 14 when the mandibular bone plate 10 is attached to the mandible 14. That is, the first extension portion 60 is rotated counterclockwise about the first axis $A_1$ relative to the chin portion 56 from the proximal end 73a and toward the distal end 73b so as to define a twisted shape such that portions of the first bone facing surface 106 face laterally outward relative to the chin bone facing surface and away from the second bone facing surface 118. For example, the first bone facing surface 106 can face away from the second bone facing surface 118 such that a line that is normal to the first bone facing surface 106 has at least a directional component that extends away from the second bone facing surface 118 along the longitudinal direction L.

Therefore it can be said that the first extension portion 60 is oriented such that a line $N_1$ that is normal to the first bone facing surface 106 at a distal portion of the first extension portion 60 is rotated about the first axis $A_1$ relative to a line $N_2$ that is normal to the first bone facing surface 106 at a proximal portion of the first extension portion 106 so that the first bone facing surface 60 is configured to abut at least a portion of at least two of the buccal, lingual and inferior surfaces of the mandible when the mandibular bone plate 10 is attached to the mandible. It can also be said that the first extension portion 60 is oriented such that a line $M_1$ that is tangential to the inferior end 106a and to the superior end 106b of the first bone facing surface 106 along the first direction at a distal portion of the first extension portion 60 is rotated about the first axis $A_1$ relative to a line $M_2$ that is tangential to the inferior end 106a and to the superior end 106b of the first bone facing surface along the first direction at a proximal portion of the first extension portion 106 so that the first bone facing surface 60 is configured to abut at least a portion of at least two of the buccal, lingual and inferior surfaces of the mandible when the mandibular bone plate 10 is attached to the mandible. It should be appreciated, that the proximal portion can be at the proximal end 73a or some portion between the proximal end 73a and distal end 73b, and the distal portion can be any portion between the proximal end 73a and the distal end 73b that is distal to the proximal portion. It should further be appreciated, that the first extension portion 60 can be twisted along a portion of a length of the first extension portion 60 and up to the entire length of the first extension portion 60. It should also be appreciated, that twisted is used to describe the orientation of the first extension portion 60 and does not necessarily mean that the first extension portion 60 was actually twisted to form the disclosed orientation. For example, the first extension portion 60 can be molded or milled to define the twisted orientation.

As shown in FIGS. 2B and 2D, the first bone facing surface 106 includes a plurality of non-linear undulations 140 that correspond to respective surface portions of the mandible 14 such as the lingual surface 22 when the mandibular bone plate 10 is attached to the mandible 14. It should be appreciated, that the first extension portion 60 can be twisted counterclockwise or otherwise rotated about the first axis $A_1$ such that the first bone facing surface 106 is configured to also abut at least a portion of the inferior surface 26 of the mandible 14 or any two of the when the mandibular bone plate 10 is attached to the mandible 14.

As shown in FIGS. 2A, 2C, 2F and 2H, the first extension portion 60 can further define a third side surface 150 that extends from the first outer surface 110 to the first bone facing surface 106 and a fourth side surface 154 that is opposite the third side surface 150 and extends from the first outer surface 110 to the first bone facing surface 106. As shown in FIG. 2H, the third and fourth side surfaces 150 and 154 can be convex or otherwise curved. As shown in FIG. 2A, the first extension portion 60 can further include a plurality of weakened portions 158 between adjacent bone anchor holes 114. The weakened portions 158 are configured to allow the first extension portion 60 to be bent during implantation of the mandibular bone plate 10 and/or to be shortened. For example, the weakened portions 158 are proximate to the distal end D of the first extension portion 60 such that the first extension portion 60 can be cut or otherwise broken at one of the weakened portions 158 to thereby shorten the first extension portion 60. Each weakened portion 158 is defined by at least a first recess 162 that extends into the third side surface 150 and a second recess 166 that extends into the fourth side surface 154 opposite the first recess 162. In the illustrated embodiment, the first extension portion 60 includes nine bone anchor holes 114 and three weakened portions 158. It should be appreciated, however, that the first extension portion 60 can include any number of bone anchor holes 114 as desired and any number of weakened portions 158 as desired. It should be further appreciated, that the weakened portions 158 can be defined by other structure. For example, the weakened portions 158 can be defined by recesses formed in the first bone facing surface 106 and/or the outer surface 110.

With continued reference to FIG. 2H, at least a portion of the first extension portion 60, up to an entirety of the first extension portion 60 can be substantially triangular shaped in cross-section. That is, the first extension portion 60 can taper from the third side surface 150 to the fourth side surface 154. Therefore a thickness of the first extension portion 60 at the fourth side surface 154 can be less than that of the first extension portion 60 at a center of the first extension portion 60 between the third and fourth side surfaces 150 and 154. It should be appreciated, however, that the first extension portion 60 can have any shape in cross-section, as desired. For example, the first extension portion 60 can be rectangular shaped in cross-section as desired.

With continued reference to FIG. 2H, the first bone facing surface 106 can be concave from the third side surface 150 to the fourth side surface 154. The concave shape can help conform the mandibular bone plate 10 to at least one of the surfaces 18, 22, and 26 of the mandible 14. It should be appreciated, however, that the first bone facing surface 106 can have any shape as desired. For example, the first bone facing surface 106 can be substantially flat as desired.

Referring back to FIGS. 2B-2D, the second extension portion 64 is twisted clockwise about the second axis $A_2$ relative to the curved chin portion 56 such that the second bone facing surface 118 is configured to abut at least a portion of the lingual surface 22 of the mandible 14 when the mandibular bone plate 10 is attached to the mandible 14. That is, the second extension portion 64 is rotated clockwise about the second axis $A_2$ relative to the chin portion 56 from the proximal end 74a and toward the distal end 74b so as to define a twisted shape such that portions of the second bone facing surface 118 face laterally outward relative to the chin bone facing surface 76 and away from the first bone facing surface 106. For example, the second bone facing surface 118 can face away from the first bone facing surface 106 such that a line that is normal to the second bone facing surface 118 has at least a directional component that extends away from the first bone facing surface 106 along the longitudinal direction L.

Therefore it can be said that the second extension portion 64 is oriented such that a line $N_3$ that is normal to the first bone facing surface 118 at a distal portion of the second extension portion 64 is rotated about the second axis $A_2$ relative to a line $N_4$ that is normal to the second bone facing surface 118 at a proximal portion of the second extension portion 64 so that the second bone facing surface 118 is configured to abut at least a portion of at least two of the buccal, lingual and inferior surfaces of the mandible when the mandibular bone plate 10 is attached to the mandible. It can also be said that the second extension portion 64 is oriented such that a line $M_3$ that is tangential to the inferior end 118a and to the superior end 118b along the second direction at a distal portion of the second extension portion 64 is rotated about the second axis $A_2$ relative to a line $M_4$ that is tangential to the inferior end 118a and to the superior end 118b along the second direction at a proximal portion of the second extension portion 64 so that the second bone facing surface 118 is configured to abut at least a portion of at least two of the buccal, lingual and inferior surfaces of the mandible when the mandibular bone plate 10 is attached to the mandible. It should be appreciated, that the proximal portion can be at the proximal end or some portion between the proximal end 74a and distal end 74b, and the distal portion can be any portion between the proximal end 74a and the distal end 74b that is distal to the proximal portion. It should further be appreciated, that the second extension portion 64 can be twisted along a portion of a length of the second extension portion 64 and up to the entire length of the second extension portion 64. It should also be appreciated, that twisted is used to describe the orientation of the second extension portion 64 and does not necessarily mean that the second extension portion 64 was actually twisted to form the disclosed orientation. For example, the second extension portion 64 can be molded or milled to define the twisted orientation.

As shown in FIGS. 2B and 2D, the second bone facing surface 118 also includes a plurality of non-linear undulations 140 that correspond to respective surface portions of the mandible 14 such as the lingual surface 22 when the mandibular bone plate 10 is attached to the mandible 14. It should be appreciated, that second extension portion 64 can be twisted clockwise about the second axis $A_2$ such that the second bone facing surface 118 is configured to also abut at least a portion of the inferior surface 26 of the mandible 14 when the mandibular bone plate 10 is attached to the mandible 14.

As shown in FIGS. 2C, 2F and 2I, the second extension portion 64 can further define a fifth side surface 180 that extends from the second outer surface 122 to the second bone facing surface 118 and a sixth side surface 184 that is opposite the fifth side surface 180 and extends from the second outer surface 122 to the second bone facing surface 118. As shown in FIG. 2I, the fifth and sixth side surfaces 118 and 122 can be convex or otherwise curved. As shown in FIG. 2F, the second extension portion 64 can further include a plurality of weakened portions 188 between adjacent bone anchor holes 128. The weakened portions 188 are configured to allow the second extension portion 64 to be bent during implantation of the mandibular bone plate 10 and/or to be shortened. For example, the weakened portions 158 are proximate to the distal end D of the second extension portion 64 such that the second extension portion 64 can be cut or otherwise broken at one of the weakened portions 188 to thereby shorten the second extension portion 64. Each weakened portion 188 is defined by at least a first recess 192 that extends into the fifth side surface 180 and a second recess 196 that extends into the sixth side surface 184 opposite the first recess 192. In the illustrated embodiment, the second extension portion 64 includes nine bone anchor holes 128 and three weakened portions 188. It should be appreciated, however, that the second extension portion 64 can include any number of bone anchor holes 128 as desired and any number of weakened portions 188 as desired. It should be further appreciated, that the weakened portions 188 can be defined by other structure. For example, the weakened portions 188 can be defined by recesses formed in the second bone facing surface 118 and/or the outer surface 122.

With continued reference to FIG. 2I, at least a portion of the second extension portion 64, up to an entirety of the second extension portion 64 can be substantially triangular shaped in cross-section. That is the second extension portion 64 can taper from the fifth side surface 180 to the sixth side surface 184. Therefore a thickness of the second extension portion 64 at the sixth side surface 184 can be less than that of a center of the second extension portion 64 between the fifth and sixth side surfaces 180 and 184. It should be appreciated, however, that the second extension portion 64 can have any shape in cross-section. For example, the second extension portion 64 can be rectangular shaped in cross-section as desired. It should be further appreciated, that substantially triangular shaped means to have the general appearance of a triangle.

With continued reference to FIG. 2I, the second bone facing surface 118 can be concave from the fifth side surface 180 to the sixth side surface 184. The concave shape can help conform the mandibular bone plate 10 to one of the surfaces 18, 22, and 26 of the mandible 14. It should be appreciated, however, that the second bone facing surface 118 can have any shape as desired. For example, the second bone facing surface 118 can be substantially flat as desired.

Now in reference to FIGS. 3A-3C, the bone anchor holes 52, such as the bone anchor holes 84 of the chin portion 56, the bone anchor holes 114 of the first extension portion 60, and the bone anchor holes 128 of the second extension portion 64 can be configured as locking or compression holes and as fixed axis or variable angle holes. As shown in FIG. 2C, each bone anchor hole 114 and 128 of the first and second extension portions 60 and 64 defines a respective central axis $A_H$, and at least some of the central axes $A_H$ are angular offset with respect to the other central axes $A_H$. Therefore, the bone anchors that are received within the holes 114 and 128 will have different trajectories as they pass through the holes 114 and 128. It should be appreciated that the bone anchor holes 52 can all or in part have central axes $A_H$ that are parallel or that converge on one or more points that define a trajectory origin or destination.

As shown in FIG. 3A, all of, some of, or none of the bone anchor holes 52 can be configured as a variable angle compression hole 210. As shown in FIG. 3A, the variable angle compression hole 210 can be defined by an interior surface 214 of the bone plate body 40. An upper portion of the interior surface 214 can be tapered radially inward toward the central axis $A_H$ from the bone facing surface 44 toward the outer surface 48 and a lower portion of the interior surface 214 can converge away from the central axis $A_H$. The interior surface 214 can be unthreaded and configured to engage an unthreaded head of a compression bone anchor or screw that provides a compressive force against the bone plate 10 in a direction toward the mandible 14. As shown in FIG. 3A, an outer region 222 of the upper portion of the interior surface 214 can be curved such that a diameter of the hole 210 decreases variably along the central axis $A_H$, an interior region 228 of the upper portion of the interior surface 214 can be linear such that the diameter of the hole 210 decreases linearly along the central axis $A_H$.

As shown in FIGS. 3B and 3C, all of, some of, or none of the bone anchor holes 44 can be configured as a variable angle locking hole 310a or 310b. As shown in FIGS. 3B and 3C, each variable angle hole 310a and 310b is defined by an interior surface 314 of the bone plate body 40. The interior surface 314 includes a plurality of columns 318 that extend between the bone facing surface 44 and the outer surface 48. In accordance with the embodiment illustrated in FIG. 3B, three columns 318 can be equidistantly spaced circumferentially about the hole 310a and in accordance with the embodiment illustrated in FIG. 3C, four columns 318 can be equidistantly spaced circumferentially about the hole 310b. It should be appreciated, however, that the holes 310a and 310b can alternatively include any number of columns as desired, spaced circumferentially equidistantly as illustrated, or at circumferentially variable distances as desired. Each column 318 presents internal threads 322 that face the respective holes 310a and 310b such that, if the columns 318 were expanded to join each other (i.e. if extended completely around the interior surface 314), the columns 318 would form a continuous helical thread that extends about the central axis $A_H$ of the respective holes 310a and 310b. Thus, it can be said that the threads 322 of adjacent columns 318 are operatively aligned with each other.

It should be appreciated that while the columns 318 present internal helical threads 322 as illustrated, the columns 318 alternatively can define threads that are provided as teeth formed thereon. The columns of teeth, if expanded to join each other (i.e., if extended completely around the interior surface 314), will not form a helical thread, but a series of concentric ridges and grooves perpendicular to the central axis $A_H$ of the bone anchor hole 52. Thus, it can be said that the teeth can be operatively aligned with each other. The columns 318 are circumferentially spaced from each other so as to define corresponding axes that are angled with respect to the transverse central axis $A_H$, such that a screw can extend through the holes 310a and 310b at any of a variety of angled axes while threadedly fixed to the threads 322.

With continued reference to FIGS. 3B and 3C, the interior surfaces 314 that define the holes 310a and 310b each further includes a plurality of arcuate pockets 330 that project into the plate body 40 at a location circumferentially between the adjacent columns 318. The pockets 330 each presents an arcuate surface 334 that is concave with respect to a direction radially outward from the central axis $A_H$ of the respective hole 310a and 310b. The variable angle holes 310a and 310b can be configured to allow the bone anchor or screw to engage the threads 318 at any angular orientation as desired, up to +/−15° (e.g., within a 30° range) with respect to the central axis $A_H$.

It should be appreciated that while the bone plate 10 is illustrated as including variable angle holes 210, 310a, and 310b extending through the bone plate body 40, the bone plate 10 can alternatively include any type of bone anchor hole 52 as desired. For example, all of or some of the bone anchor holes 52 can be configured as fixed axis holes.

Figure 4A:
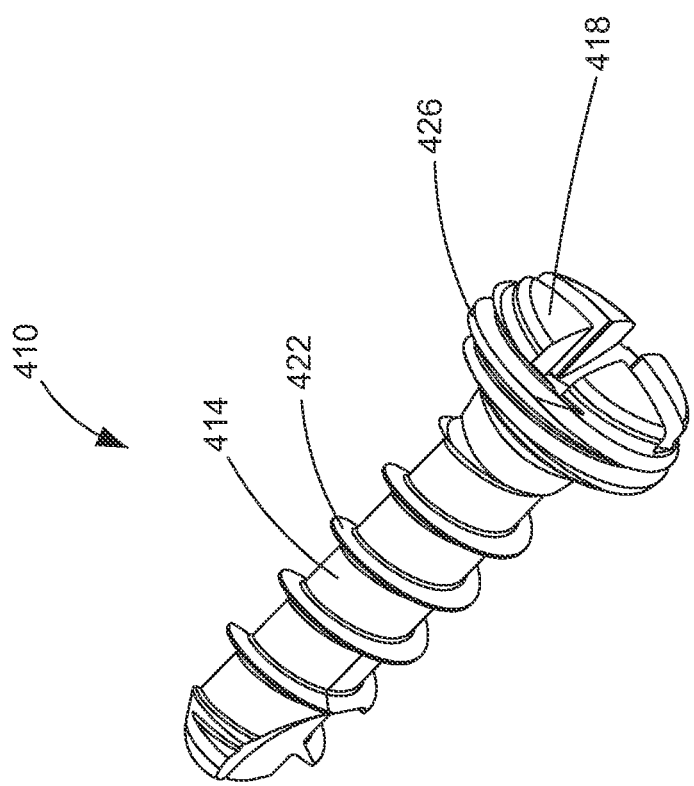
FIG. 4A is an example embodiment of a bone anchor that may be used to attach the mandibular bone plate to the mandible, the bone anchor being configured as a locking screw.

As shown in FIG. 4A, a bone anchor such as a screw 410 can be used to affix or otherwise attach the mandibular bone plate 10 to the mandible 14. As shown, the screw 410 can include a shaft 414 and a head 418 that extends from the shaft 414. The shaft 414 can carry a thread 422 that is configured to engage bone to thereby attach the bone plate 10 to the mandible 14. The head 418 can also carry a thread 426 that is configured to engage the threads 322 of the holes 310a or 310b to thereby lock the bone screw 410 to the bone plate 10. The screw 410 can be configured as a variable angle screw so that the screw 410 can be inserted through the holes 310a and 310b at a variety of angles. It should be appreciated, however, that the screw 410 can be configured as a fix angle screw as desired. It should further be appreciated, that the screw 410 can be configured as a compression screw. For example, the screw 410 can include a head 418 that is void of threads 426 such that the head 418 defines a surface that abuts against the outer region 222 of the bone anchor hole 210 when the screw 410 is passed through one of the holes 210 and into the mandible 14. It should be even further appreciated, that the mandibular bone plate 10 can be affixed or otherwise attached to the mandible 14 with any type of bone anchor or screw as desired. For example, pins, rivets, k-wires, etc.

Figure 4C:
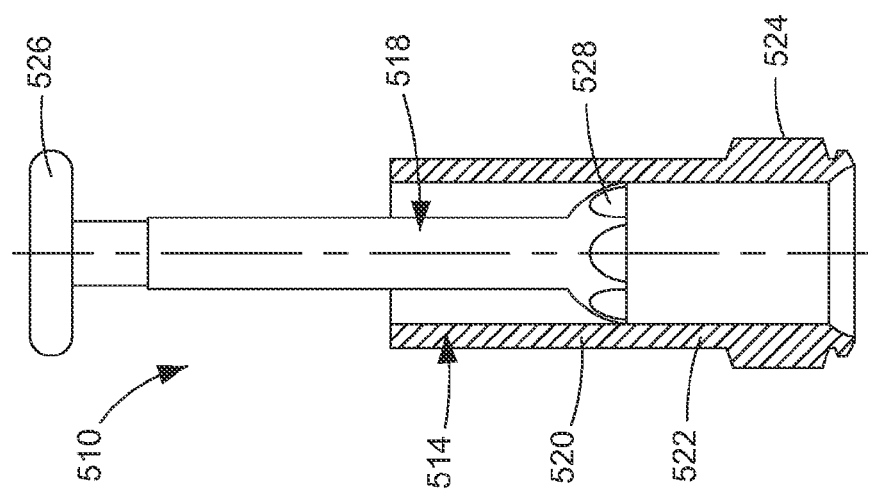
FIG. 4C is the expandable fixation member of FIG. 4B in an expanded configuration.
Figure 4B:
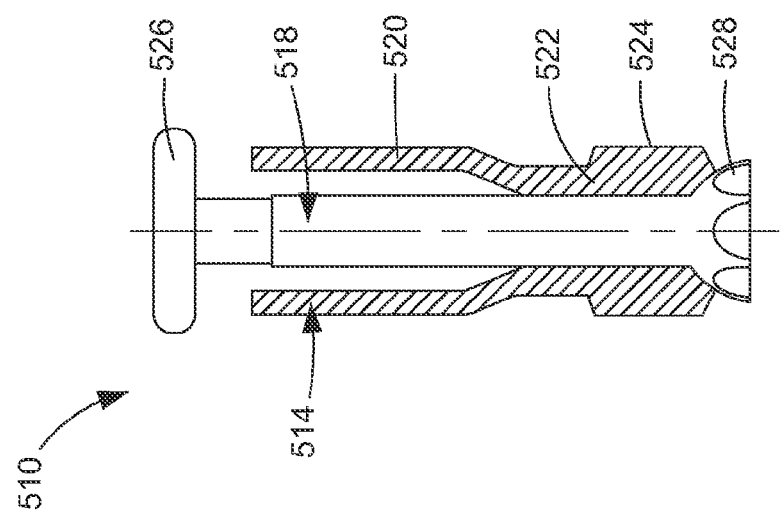
FIG. 4B is another example embodiment of a bone anchor that may be used to attach the mandibular bone plate to the mandible, the bone anchor being configured as an expandable fixation member having a cannulated shaft and an expansion member that is configured to expand the shaft.

As shown in FIGS. 4B and 4C, a bone anchor such as an expandable fixation member 510 can be used to affix or otherwise attach the mandibular bone plate 10 to the mandible 14. As shown in FIGS. 4A and 4B, the expandable fixation member 510 can include a cannulated or annular shaft 514 and an expansion member 518 that extends through the cannulated shaft 514. The shaft 514 can include a body 520 that define an expandable region 522 at its distal end. The shaft 514 can further include a shoulder 524 that extends radially out from the body 520 at the expandable region 522. The expansion member 518 can include a head 526 at a proximal end and a mandrel 528 at a distal end. When the expansion member 518 is pulled proximally relative to the shaft 514, the mandrel 528 will enter the cannulation of the shaft 514 to thereby cause the expandable region 522 to expand radially outward as shown in FIG. 4C. The expanded expandable region 522 places the shoulder 524 further radially outward. It should be appreciated, that the expandable fixation member 510 can have a variety of configurations. For example, the expandable fixation member 510 can have any of the configurations disclosed in United States Publication No 2011/0046682, assigned to Synthes USA, LLC, the contents of which are hereby incorporated by reference in their entirety herein.

Now in reference to FIGS. 5A-5F, the mandibular bone plate 10 can be attached to the mandible 14 such that portions of the bone plate 10 face the inferior surface 26 of the mandible and portions of the bone plate 10 face the lingual surface 22 of the mandible 14. In particular, the inferior 26 and lingual 22 surfaces of the mandible 14 can be exposed and the bone plate 10 can be positioned against the mandible such that portions of the bone plate 10 abut the lingual surface 22 of the mandible 14. The bone plate 10 can then be attached to the mandible 14 with a plurality of bone anchors such as screws 410. In this way the mandibular bone plate 10 can be positioned against the mandible 14 from a submandibular surgical approach. It should be appreciated, however, that the mandibular bone plate 10 can be positioned from any desired approach.

Figure 5A:
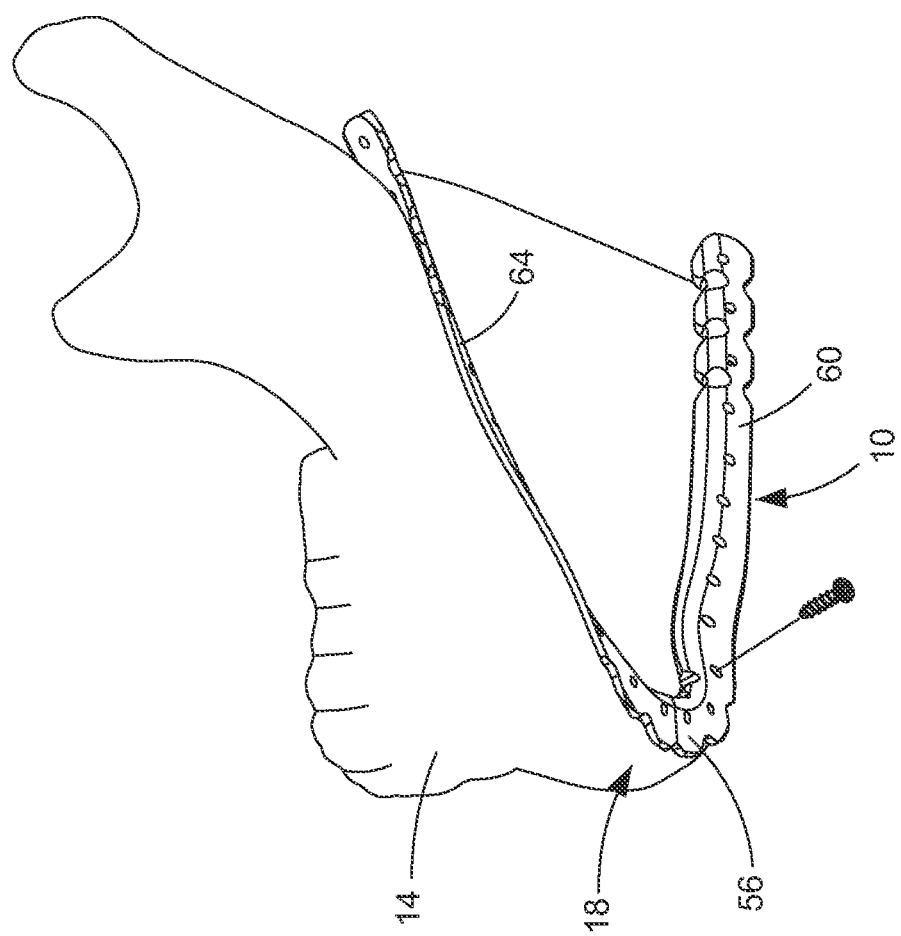
FIG. 5A is a bottom perspective view of the mandibular bone plate shown in FIG. 2A attached to the mandible shown in FIG. 1A.
Figure 5B:
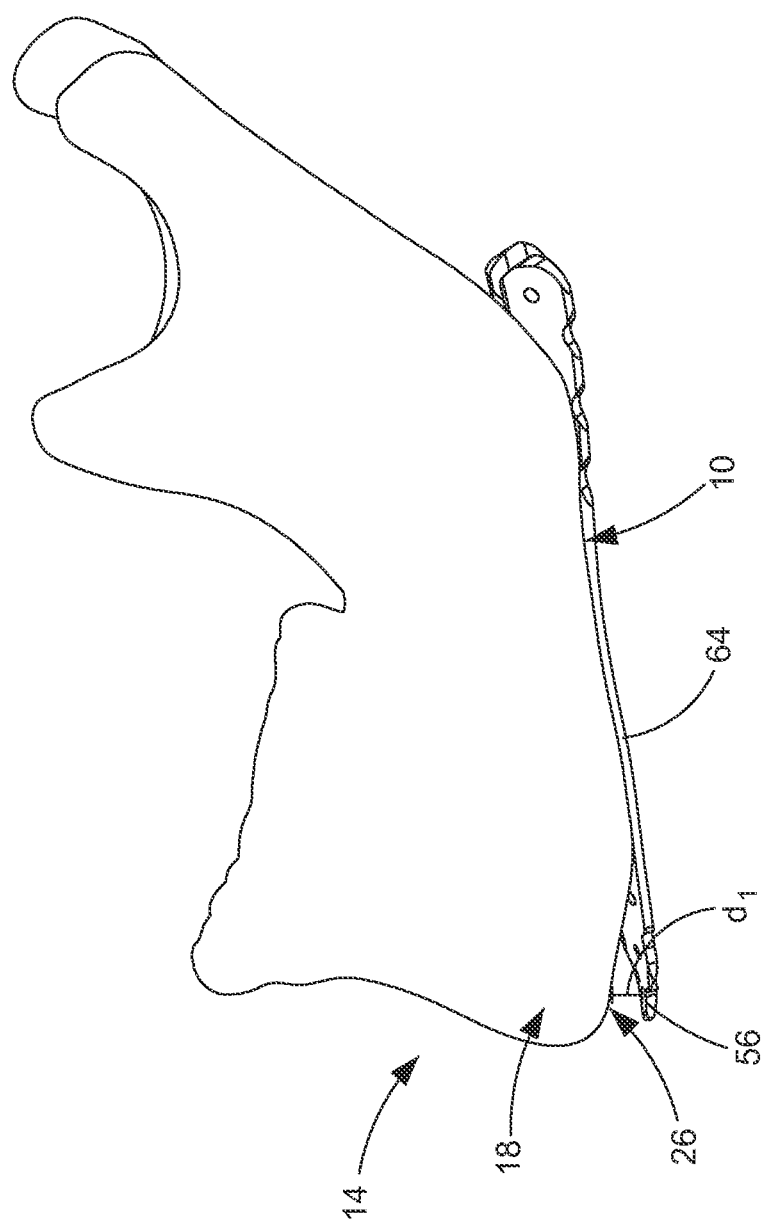
FIG. 5B is a side elevation view of the mandibular bone plate shown in FIG. 2A attached to the mandible shown in FIG. 1A.

As shown in FIGS. 5B-5F, the mandibular bone plate 10 can be positioned such that portions of the bone plate 10 abut the lingual surface 22 and at least one portion of the bone plate 10 faces the inferior surface 26 of the mandible 14. As shown in FIG. 5B, the chin portion 56 can face the inferior surface 26 such that the chin bone facing surface 76 is spaced from the inferior surface 26 by a distance $d_1$. It should be appreciated, however, that the chin bone facing surface 76 can abut the inferior surface 26 as desired.

Figure 5D:
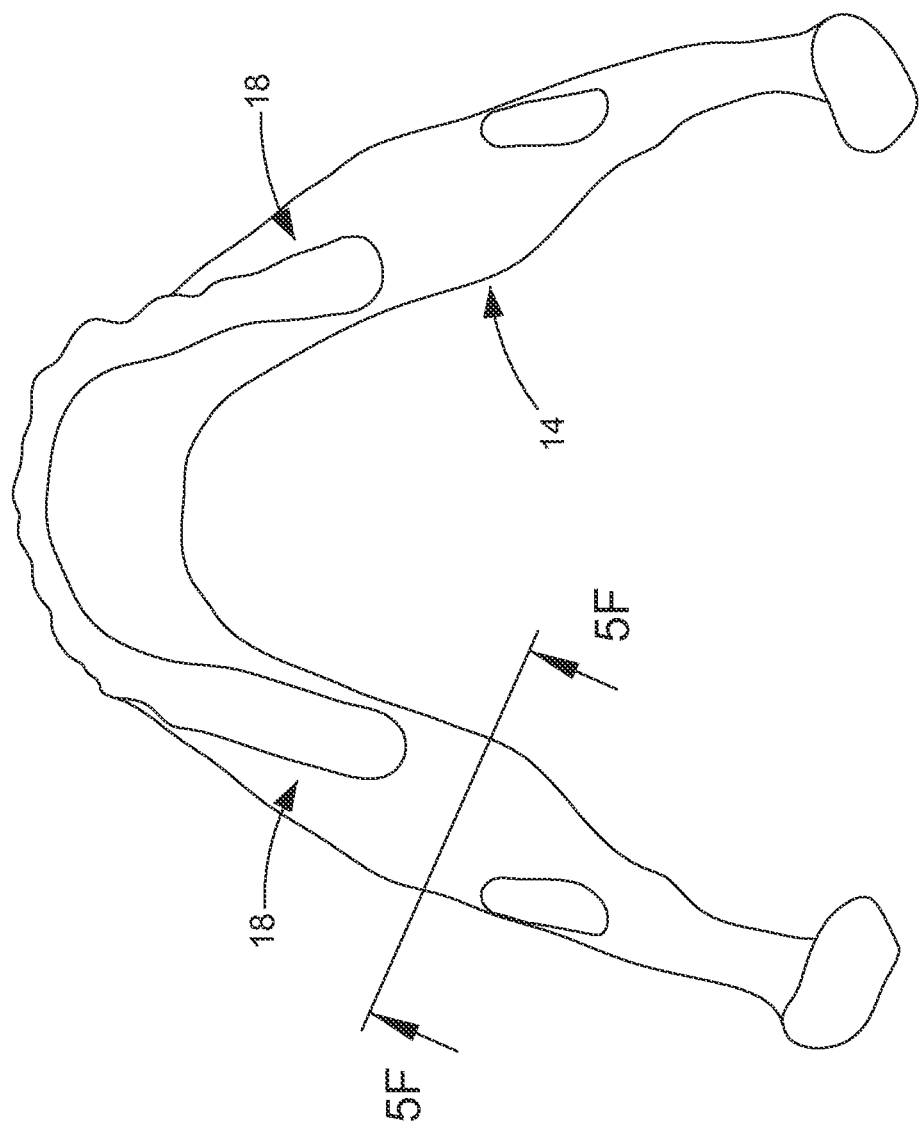
FIG. 5D is a top plan view of the mandibular bone plate shown in FIG. 2A attached to the mandible shown in FIG. 1A.
Figure 5E:
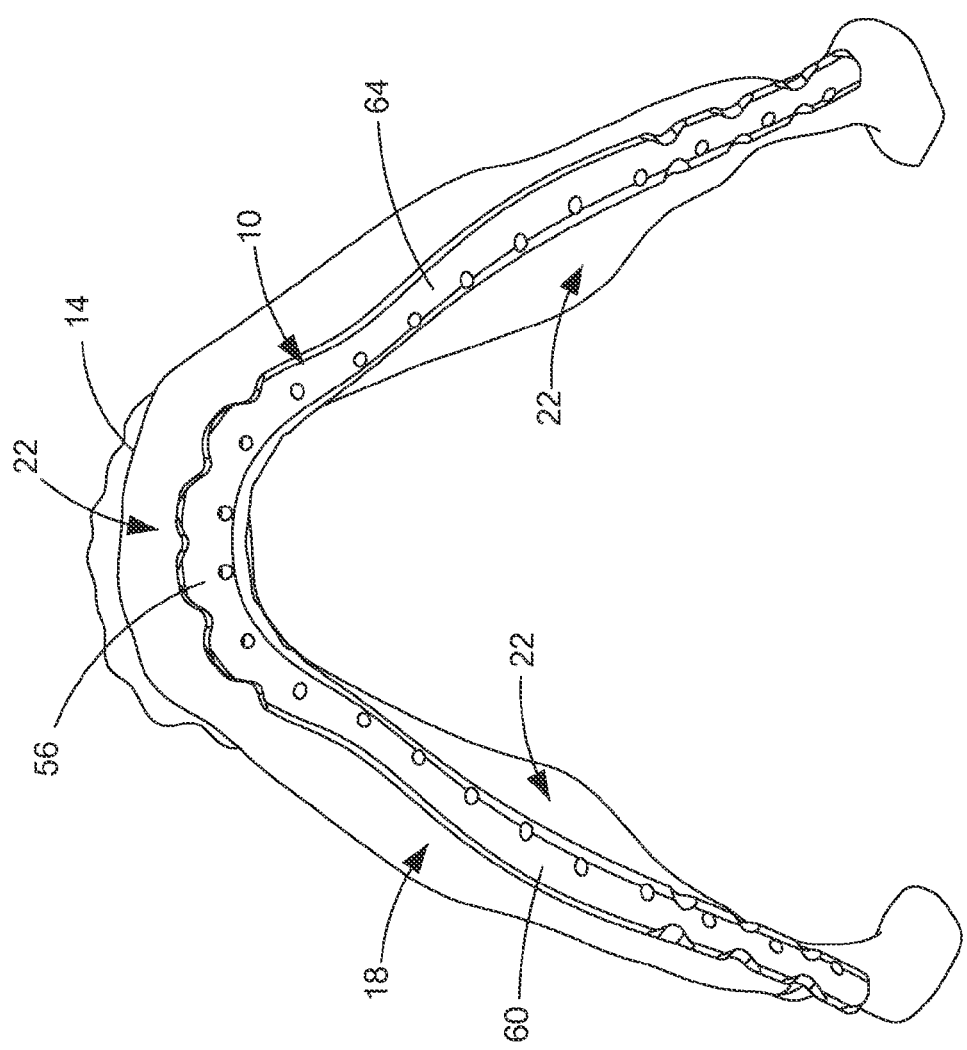
FIG. 5E is a bottom plan view of the mandibular bone plate shown in FIG. 2A attached to the mandible shown in FIG. 1A.

As shown in FIGS. 5D-5F, the first and second bone facing surfaces 106 and 118 can abut both the lingual surface 22 and the inferior surface 26. As shown in FIG. 5F, the bone plate 10 is positioned such that the extension portions 60 and 64 taper as they extend from the lingual surface 22 and toward the buccal surface 18. Because of the positioning of the first and second extension portions 60 and 64 and because of the taper of the first and second extension portions 60 and 64, the palpability of the mandibular bone plate 10 can be reduced. It should be appreciated, however, that the mandibular bone plate 10 can be configured so as to abut the buccal and inferior surfaces 18 and 26 or can be configured to abut all three surfaces 18, 22, and 26 such that the taper of the extension portions 60 and 64 achieves the reduced palpability.

Prior to or during the positioning of the bone plate 10, the bone plate 10 can be shortened by cutting the first and second extension portions 60 and 64 at the weakened portions 158 and 188. Further prior to or during the positioning of the bone plate 10, the bone plate 10 can be bent or otherwise manipulated at any of the weakened portions 96, 158, and 188 of the chin portion 56, first extension portion 60, and second extension portion 64 to thereby better conform the bone plate 10 to the mandible 14.

Figure 6:
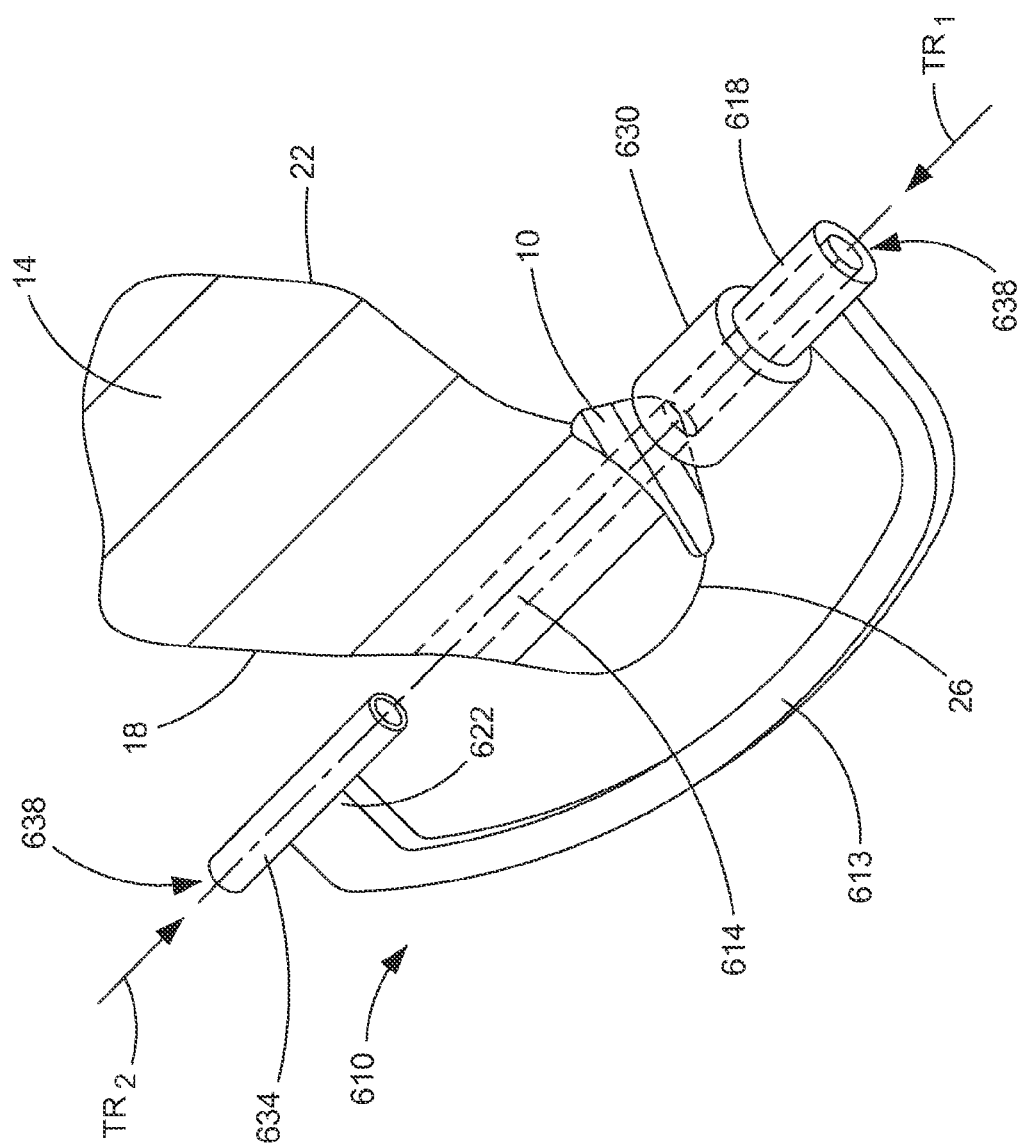
FIG. 6 is a schematic of an example drill guide configured to be used to form holes in the mandible.

Now in reference to FIG. 6, a drill guide 610 can be used to form holes 614 in the mandible 14. The drill guide 610 can be configured as a bi-directional drill guide that is capable of aligning a drill bit such that the holes 614 can be drilled into the buccal surface 18 of the mandible 14 and toward either the lingual surface 22 or the inferior surface 26 or such that holes 614 can be drilled into the lingual or inferior surfaces 22 and 26 and toward the buccal surface 18. As shown in FIG. 6, the drill guide 610 can include a C-shaped body 616 having a first end 618 and a second end 622 spaced from the first end along a first direction. The drill guide 610 can further include a first guide portion 630 coupled to the first end 618 and a second guide portion 634 coupled to the second end 622. The first and second guide portions 630 and 634 can each define a respective guide path 638 that extends through the first and second guide portions 630 and 634 along the first direction such that the guide paths 638 of the first and second guide portions 630 and 634 are aligned along the first direction.

As shown in FIG. 6, the drill guide 610 can be positioned such that the first guide portion 630 is aligned with a bone anchor hole 52 of the mandibular bone plate 10 and the second guide portion 634 is aligned with the buccal surface 18 of the mandible 14. A drill bit can then be moved through either the guide path 638 of the first guide portion 630 or through the guide path 638 of the second guide portion 634 to thereby form a hole 614 in the mandible 14. In this way the drill bit can have a first trajectory $TR_1$ through the first guide portion 630 and a second trajectory $TR_2$ through the second guide portion 634 that is opposite the first trajectory $TR_1$. The guide paths 638 are oriented so that when the drill guide 610 is positioned adjacent the bone plate 10 and the mandible 14 a drill bit boring into the mandible 14 will avoid nerves or other soft tissue.

Figure 7:
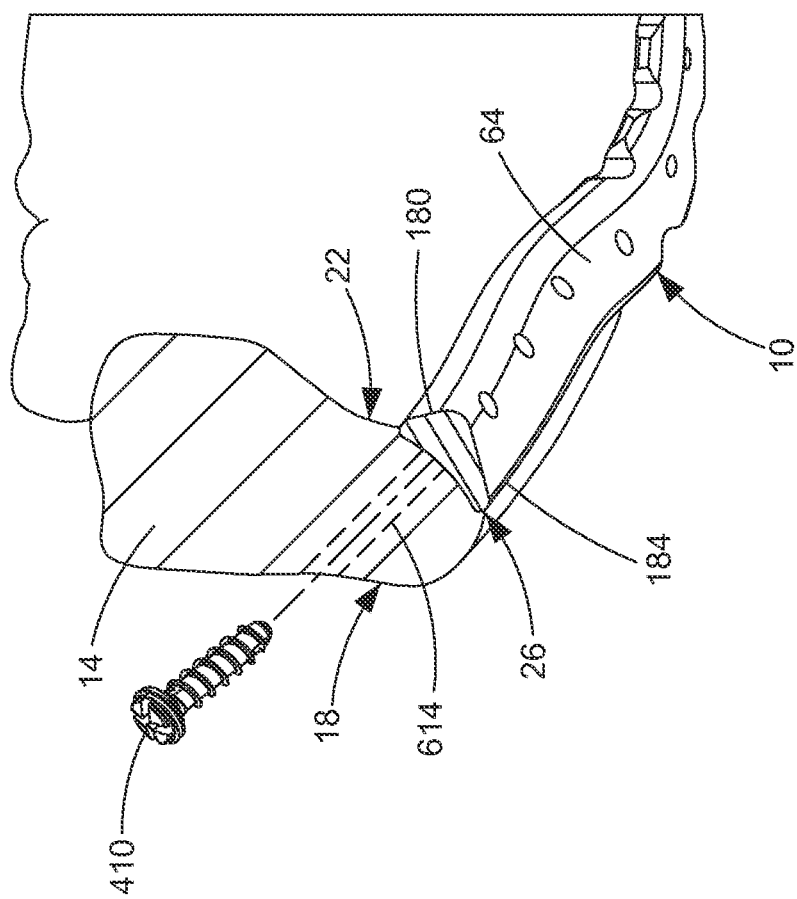
FIG. 7 is a cross-sectional view of a bone anchor being inserted through the buccal surface of the mandible and into the mandibular bone plate to thereby attach the bone plate to the mandible.

As shown in FIG. 7, the mandibular bone plate 10 can be attached to the mandible 14 by inserting a bone anchor such as a screw 410 through the buccal surface 18 and into one of the bone anchor holes 52 of the bone plate 10. Therefor it should be appreciated, that the bone plate 10 can be attached to the mandible 14 from a variety of trajectories including from the lingual surface toward the buccal surface or inferior surface, the buccal surface toward the lingual surface or the inferior surface, and the inferior surface toward the lingual surface or buccal surface.

Figure 8:
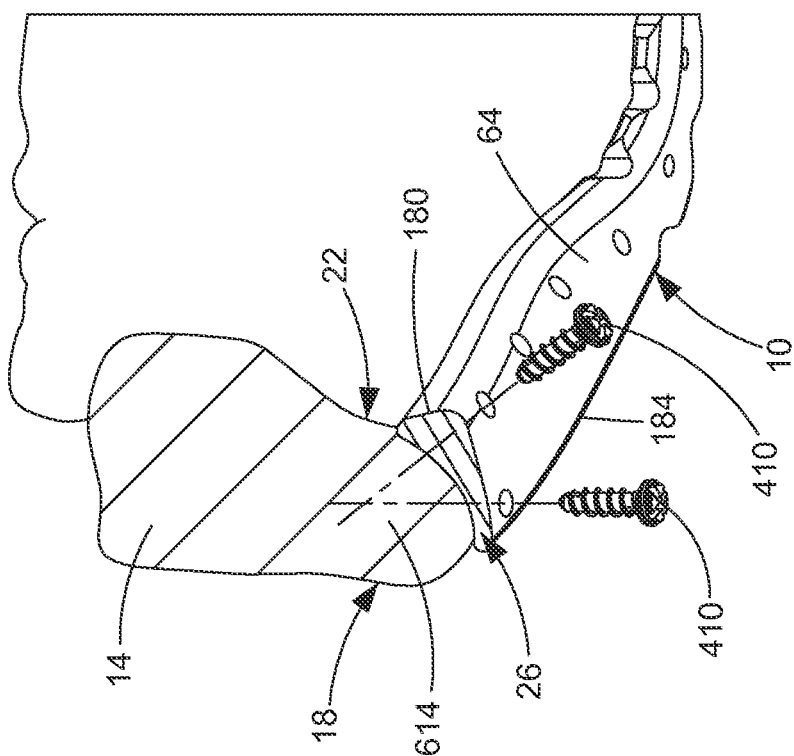
FIG. 8 is a cross-sectional view of a bone anchor being inserted through the bone plate and into the inferior surface of the mandible and a bone anchor being inserted through the bone plate and into the lingual surface of the mandible.

As shown in FIG. 8, the bone anchor holes 52 of the mandibular bone plate 10 can be configured to provide an interstitially spaced hole pattern. For example, a first bone anchor hole such as hole 52a can be positioned such that a bone anchor received within the first bone anchor hole extends into the inferior surface 26 of the mandible and a second bone anchor hole such as hole 52b can be positioned such that a bone anchor received within the second bone anchor hole extends into the lingual surface 22. Because the trajectory of the bone anchors through the first and second holes 52a and 52b are different the prospect of the plate 10 backing out or otherwise moving from its desired position is reduced. It should be appreciated that the holes 52 can be positioned such that the bone anchors have any trajectory as desired and extend into any surface of the mandible as desired.

The mandibular bone plate 10 along with at least one such as a plurality of bone anchors, and/or the drill guide 610 can be provided as a kit. Therefore, the bone plate 10, along with any of the bone anchors 410 and/or 510, and/or the drill guide 610 can be provided as a kit. It should be appreciated, however, that the bone plate 10 or drill guide 610 can be provided as a kit with any desired components.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A mandibular bone plate configured to be attached to a mandible that defines a buccal surface, a lingual surface, and an inferior surface that joins the buccal surface to the lingual surface, the mandibular bone plate comprising:
   a monolithic body that defines a bone facing surface, an outer surface that is opposite the bone facing surface, and a plurality of bone anchor holes that extend through the body from the bone facing surface to the outer surface, the body including:
   a chin portion, a first extension portion, and a second extension portion, the chin portion defining a portion of the bone facing surface that faces in a first direction, wherein the first and second extension portions each extend from the chin portion such that:
   i) a first portion of the bone facing surface defined by the first extension portion: 1) faces away from a first portion of the bone facing surface defined by the second extension portion, and 2) is spaced from the first portion of the second extension portion by a first distance measured in a second direction that is perpendicular to the first direction;
   ii) a second portion of the bone facing surface defined by the first extension portion: 1) faces away from a second portion of the bone facing surface defined by the second extension portion, and 2) is spaced from the second portion of the second extension portion by a second distance that is measured in the second direction, such that the second distance is greater than the first distance; and
   wherein the portion of the bone facing surface defined by the chin portion is configured to face the inferior surface of the mandible when the mandibular bone plate is attached to the mandible, the first and second portions of the bone facing surface defined by the first and second extension portions are configured to at least partially face the lingual surface of the mandible when the mandibular bone plate is attached to the mandible, and the bone facing surface is continuous from the first extension portion, through the chin portion, and through the second extension portion.

2. The mandibular bone plate of claim 1, wherein the chin portion is curved and defines a first end and a second end that is opposite the first end, and wherein the first extension portion extends from the first end along a first axis and is elongate along the first axis and the second extension portion extends from the second end along a second axis and is elongate along the second axis.

3. The mandibular bone plate of claim 2, wherein the first extension portion is twisted counterclockwise about the first axis relative to the curved chin portion such that the bone facing surface of the first extension portion is configured to abut at least a portion of the lingual surface of the mandible when the mandibular bone plate is attached to the mandible and the second extension portion is twisted clockwise about the second axis relative to the curved chin portion such that the bone facing surface of the second extension portion is configured to abut at least a portion of the lingual surface of the mandible when the mandibular bone plate is attached to the mandible.

4. The mandibular bone plate of claim 1, wherein the bone facing surfaces of the first and second extension portions each includes a plurality of undulations that correspond to respective portions of the lingual surface of the mandible when the mandibular bone plate is attached to the mandible.

5. The mandibular bone plate of claim 4, wherein the chin portion has a reduced thickness relative to the first and second extension portions.

6. The mandibular bone plate of claim 1, wherein the chin portion defines a first side surface that extends from the outer surface to the bone facing surface and a second side surface that is opposite the first side surface and extends from the outer surface to the bone facing surface, (ii) the first extension portion defines a third side surface that extends from the outer surface to the bone facing surface and a fourth side surface that is opposite the third side surface and extends from the outer surface to the bone facing surface, and (iii) the second extension portion defines a fifth side surface that extends from the outer surface to the bone facing surface and a sixth side surface that is opposite the fifth side surface and extends from the outer surface to the bone facing surface.

7. The mandibular bone plate of claim 6, wherein at least a portion of the first extension portion is tapered from the third side surface to the fourth side surface and at least a portion of the second extension portion is tapered from the fifth side surface to the sixth side surface.

8. The mandibular bone plate of claim 6, wherein the first and second extension portions each defines a respective first recess that extends into the third and fifth side surfaces, respectively, between adjacent bone anchor holes and a respective second recess that extends into the fourth and sixth side surfaces, respectively, between the adjacent bone anchor holes opposite the respective first recesses.

9. The mandibular bone plate of claim 1, wherein the first and second extension portions each includes at least one weakened portion between adjacent bone anchor holes.

10. The mandibular bone plate of claim 1, wherein the chin portion includes at least two bone anchor holes of the plurality of bone anchor holes and at least one weakened portion between adjacent bone anchor holes of the at least two bone anchor holes.

11. The mandibular bone plate of claim 1, wherein the first and second extension portions each extend from the chin portion along first and second axes, respectively, and wherein at least a portion of the first and second extension portions are substantially triangular shaped in cross-section along a plane that is perpendicular to the first and second axes.

12. The mandibular bone plate of claim 1, wherein the bone facing surfaces of the first and second extension portions are concave.

13. The mandibular bone plate of claim 1, wherein the first and second extension portions each extend from the chin portion along first and second axes, respectively, and wherein the first and second extension portions are twisted about the first and second axes, respectively, such that the first and second bone facing surfaces are configured to abut at least a portion of the inferior surface and at least a portion of the lingual surface of the mandible when the mandibular bone plate is attached to the mandible.

14. The mandibular bone plate of claim 1, wherein the first and second extension portions each extend from the chin portion along first and second axes, respectively, and wherein each bone anchor hole of the body defines a respective central axis, and at least some of the central axes are angularly offset with respect to the other axes.

15. The mandibular bone plate of claim 1, wherein the first and second extension portions each extend from the chin portion such that a portion of the outer surface in the first extension portion faces toward a portion of the outer surface in the second extension portion.

16. The mandibular bone plate of claim 6, wherein the first side surface, third side surface, and fifth side surface each are devoid of holes.

17. The mandibular bone plate of claim 16, wherein the second side surface, fourth side surface, and sixth side surface each are devoid of holes.

18. The mandibular bone plate of claim 6, the chin portion defining a first end and a second end that is opposite the first end, and the first extension portion extends from the first end along a first axis such that the first extension portion is elongate along the first axis, and the second extension portion extends from the second end along a second axis such that the second extension portion is elongate along the second axis, wherein: i) the first extension portion defines a cross-sectional plane, the first axis is normal to the cross-sectional plane, and the first extension portion defines a continuous outer perimeter on the cross-sectional plane along the outer, bone-facing, third, and fourth side surfaces, and ii) the second extension portion defines cross-sectional plane, the second axis is normal to the cross-sectional plane, and the second extension portion defines continuous outer perimeter on the cross-sectional plane along the outer, bone-facing, fifth, and sixth side surfaces.

19. The mandibular bone plate of claim 18, wherein the cross-sectional plane of the first extension portion is offset from all holes defined by the first extension portion that extend along a third direction that is parallel to the first axis.

20. The mandibular bone plate of claim 19, wherein the cross-sectional plane of the second extension portion is offset from all holes defined by the second extension portion that extend along a fourth direction that is parallel to the second axis.

21. The mandibular bone plate of claim 1, wherein the first portion of the bone facing surface defined by the first extension portion is spaced from the chin portion by a third distance, the second portion of the bone facing surface defined by the first extension portion is spaced from the chin portion by a fourth distance, and the third distance is less than the fourth distance.

22. The mandibular bone plate of claim 1, wherein the first portion of the bone facing surface defined by the first extension portion is spaced from the chin portion by a third distance, the second portion of the bone facing surface defined by the first extension portion is spaced from the chin portion by a fourth distance, and the third distance is substantially equal to the fourth distance.

23. A mandibular bone plate configured to be attached to a mandible that defines a buccal surface, a lingual surface, and an inferior surface that joins the buccal surface to the lingual surface, the mandibular bone plate comprising:
   a curved chin portion having a first end and a second end; and
   a first extension portion that extends from the first end along a first axis and is elongate along the first axis so as to define a proximal end that is proximate the first end and a distal end that is spaced from the proximal end along the first axis, the first extension portion defining a concave bone facing surface, a first outer surface that is opposite the concave bone facing surface, and a plurality of bone anchor holes that extend from the concave bone facing surface to the first outer surface, the concave bone facing surface having an inferior end that is curved and a superior end that is curved, the superior end spaced from the inferior end along a first direction that is perpendicular to the first axis, the first extension portion being oriented such that a first straight line can be drawn that is tangential to both the inferior end and the superior end of the concave bone facing surface along the first direction at a distal portion of the first extension portion, the first straight line is rotated about the first axis relative to a second straight line that can be drawn that is tangential to both the inferior end and the superior end of the concave bone facing surface along the first direction at a proximal portion of the first extension portion so that the concave bone facing surface is configured to abut at least a portion of at least two of the buccal, lingual and inferior surfaces of the mandible when the mandibular bone plate is attached to the mandible.

24. The mandibular bone plate of claim 23, wherein the curved bone facing surface is a first concave bone facing surface, the mandibular bone plate further comprising a second extension portion that extends from the second end along a second axis and is elongate along the second axis so as to define a proximal end that is proximate the second end and a distal end that is spaced from the proximal end along the second axis, the second extension portion defining a second concave bone facing surface, a second outer surface that is opposite the first concave bone facing surface, and a plurality of bone anchor holes that extend from the second concave bone facing surface to the second outer surface, the second concave bone facing surface having an inferior end that is curved and a superior end that is curved, the superior end spaced from the inferior end along a second direction that is perpendicular to the second axis, the second extension portion being oriented such that a third straight line can be drawn that is tangential to the inferior end and the superior end of the second concave bone facing surface along the second direction at a distal portion of the second extension portion, the third straight line is rotated about the second axis relative to a fourth straight line that can be drawn that is tangential to the inferior end and the superior end of the second concave bone facing surface along the second direction at a proximal portion of the second extension portion so that the second concave bone facing surface is configured to abut at least a portion of at least two of the buccal, lingual, and inferior surfaces of the mandible when the mandibular bone plate is attached to the mandible.

25. The mandibular bone plate of claim 24, wherein the curved chin portion defines a chin bone facing surface, an outer surface that is opposite the chin bone facing surface, and at least one bone anchor hole that extends through the curved chin portion from the chin bone facing surface to the outer surface.

26. The mandibular bone plate of claim 25, wherein the chin bone facing surface, the first concave bone facing surface, and the second concave bone facing surface are coincident so as to define a continuous bone facing surface.

27. The mandibular bone plate of claim 26, wherein the first and second concave bone facing surfaces each includes a plurality of undulations that correspond to respective portions of the lingual surface of the mandible when the mandibular bone plate is attached to the mandible.

28. The mandibular bone plate of claim 27, wherein the curved chin portion is oriented such that the chin bone facing surface is configured to face the inferior surface of the mandible when the mandibular bone plate is attached to the mandible.

29. The mandibular bone plate of claim 25, wherein (i) the chin portion defines a first side surface that extends from the outer surface to the chin bone facing surface and a second side surface that is opposite the first side surface and extends from the outer surface to the chin bone facing surface, (ii) the first extension portion defines a third side surface that extends from the first outer surface to the first concave bone facing surface and a fourth side surface that is opposite the third side surface and extends from the first outer surface to the first concave bone facing surface, and (iii) the second extension portion defines a fifth side surface that extends from the second outer surface to the second concave bone facing surface and a sixth side surface that is opposite the fifth side surface and extends from the second outer surface to the second concave bone facing surface.

30. The mandibular bone plate of claim 29, wherein at least a portion of the first extension portion is tapered from the third side surface to the fourth side surface and at least a portion of the second extension portion is tapered from the fifth side surface to the sixth side surface.

31. The mandibular bone plate of claim 29, wherein the first and second extension portions each defines a respective first recess that extends into the third and fifth side surfaces, respectively, between adjacent bone anchor holes and a respective second recess that extends into the fourth and sixth side surfaces, respectively, between the adjacent bone anchor holes opposite the respective first recesses.

32. The mandibular bone plate of claim 24, wherein the first and second extension portions each includes at least one weakened portion between adjacent bone anchor holes.

33. The mandibular bone plate of claim 24, wherein the curved chin portion includes a plurality of bone anchor holes and at least one weakened portion between adjacent bone anchor holes.

34. The mandibular bone plate of claim 24, wherein at least a portion of each of the first and second extension portions is substantially triangular shaped in cross-section along a plane that is perpendicular to the first and second axes.

35. The mandibular bone plate of claim 24, wherein the first and second concave bone facing surfaces are concave.

36. The mandibular bone plate of claim 24, wherein the first and second extension portions are twisted about the first and second axes, respectively, such that the first and second concave bone facing surfaces are configured to abut at least a portion of the inferior surface and at least a portion of the lingual surface of the mandible when the mandibular bone plate is attached to the mandible.

37. The mandibular bone plate of claim 23, wherein each bone anchor hole of the first and second extensions defines a respective central axis, and at least some of the central axes are angularly offset with respect to the other axes.

* * * * *